United States Patent [19]

Moriya et al.

[11] Patent Number: 4,797,484

[45] Date of Patent: Jan. 10, 1989

[54] PROCESS FOR THE PREPARATION OF N'-SULPHONYL- AND N',N"-BIS-SULPHONYL-GUANIDINE DERIVATIVES

[75] Inventors: Koichi Moriya, Hachioji, Japan; Theodor Pfister, Monheim, Fed. Rep. of Germany; Hans-Jochem Riebel, Wuppertal, Fed. Rep. of Germany; Ludwig Eue, Levekusen, Fed. Rep. of Germany; Robert R. Schmidt; Klaus Lürssen, both of Bergisch-Gladbach,, Fed. Rep. of Germany

[73] Assignee: Bayer Aktiengesellschaft, Leverkusen, Fed. Rep. of Germany

[21] Appl. No.: 5,800

[22] Filed: Jan. 16, 1987

Related U.S. Application Data

[60] Continuation-in-part of Ser. No. 853,822, Apr. 18, 1986, Pat. No. 4,721,785, which is a division of Ser. No. 578,345, Feb. 9, 1984, Pat. No. 4,602,938.

[30] Foreign Application Priority Data

Mar. 4, 1983 [DE]  Fed. Rep. of Germany ....... 3307679
Sep. 23, 1983 [DE]  Fed. Rep. of Germany ....... 3334455

[51] Int. Cl.$^4$ ................ C07D 251/26; C07D 215/16; C07D 213/62
[52] U.S. Cl. .................... 544/215; 544/216; 544/217; 544/218; 544/219; 544/298; 544/300; 544/310; 544/316; 544/317; 544/319; 544/320; 544/322; 544/324; 544/328; 544/331; 546/153; 546/155; 546/156; 546/157; 546/261; 546/275; 546/283; 546/284
[58] Field of Search ............... 544/211, 212, 180, 333, 544/335, 215, 216, 217, 218, 219, 298, 300, 310, 316, 317, 319, 320, 322, 324, 328, 331; 546/153, 155, 156, 157, 261, 275, 283, 284

[56] References Cited

PUBLICATIONS

Merck et al., 9th Ed., 1976, ONR-44 (Hinsberg Synthesis).
Desulfurization with Raney Nickel. II. Sulfonamides[1,2], George R. Pettit and Raymond E. Kadunce, J. Org. Chem., vol. 27 (Dec. 1962), pp. 4566–4570.
J. Org. Chem, vol. 39, No. 24 (1974), DeChristopher, Adamek, Lyon, Klein and Baumgauten, pp. 3525–3532.

Primary Examiner—Mary C. Lee
Assistant Examiner—J. Richter
Attorney, Agent, or Firm—Sprung Horn Kramer & Woods

[57] ABSTRACT

A process for the preparation of a guanidine derivative of the formula

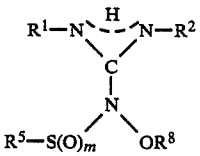

in which
$R^1$ represents hydrogen or the radical $R^5-S(O)_m-$,
m represents the numbers zero, 1 or 2 and
$R^5$ represents an optionally substituted radical from the series comprising alkyl, aralkyl, aryl and heteroaryl,
$R^2$ represents a six-membered aromatic heterocyclic structure which contains at least one nitrogen atom and is substituted, and
$R^8$ represents an optionally substituted radical from the series comprising $C_1-C_6$-alkyl, alkenyl, alkinyl, cycloalkyl, phenylalkyl and aryl, which comprises reacting a guanidine derivative of the formula

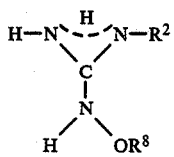

with one or two molar equivalent(s), respectively, of a halogen/sulphur compound of the formula

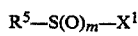

in which
$X^1$ represents fluorine, chlorine or bromine.
The compounds are herbicidally active.

11 Claims, No Drawings

PROCESS FOR THE PREPARATION OF N'-SULPHONYL- AND N',N"-BIS-SULPHONYL-GUANIDINE DERIVATIVES

This is a continuation-in-part of application Ser. No. 853,822, filed Apr. 18, 1986, now U.S. Pat. No. 4,721,785, which is a division of application Ser. No. 578,345, filed Feb. 9, 1984, now U.S.Pat. No. 4,602,938.

The invention relates to new guanidine derivatives, several processes for their preparation and their use as herbicides and plant growth regulators.

Patent Specifications (see, for example, DE-AS (German Published Specification) No. 1,089,210 and East German Patent Specification Nos. 71,016 and 84,530) have disclosed that various guanidines are potential herbicides, but these compounds have been relatively unimportant hitherto as agents for combating weeds and/or regulating plant growth.

New guanidine derivatives of the general formula (I)

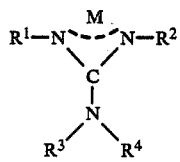

have been found, in which
R$^1$ represents hydrogen or the radical —S(O)$_m$—R$^5$,
wherein
m represents the numbers zero, 1 or 2 and
R$^5$ represents an optionally substituted radical from the series comprising alkyl, aralkyl, aryl and heteroaryl,
R$^2$ represents a six-membered aromatic heterocyclic structure which contains at least one nitrogen atom and is substituted by halogen, amino, cyano or formyl and/or by optionally substituted radicals from the series comprising alkyl, alkoxy, alkylamino, dialkylamino, alkylcarbonyl and alkoxycarbonyl, and/or is optionally fused,
R$^3$ represents hydrogen, an optionally substituted radical from the series comprising alkyl, cycloalkyl, alkenyl, alkinyl and aralkyl, or the radical —S(O)$_n$—R$^6$,
wherein
n represents the numbers zero, 1 or 2 and
R$^6$ represents an optionally substituted radical from the series comprising alkyl, aralkyl, aryl and heteroaryl,
R$^4$ represents hydrogen or hydroxyl, with the proviso that then at least one of the radicals R$^1$ and/or R$^3$ is not hydrogen;
and in which furthermore—in the case in which R$^3$ is not hydrogen—
R$^4$ represents an optionally substituted radical from the series comprising alkyl, alkenyl, alkinyl, cycloalkyl, aralkyl and aryl, or
R$^3$ and R$^4$ together represent alkanediyl which is optionally interrupted by an oxygen atom or by a bridge >N—R$^7$,
wherein
R$^7$ represents optionally substituted alkyl, alkylcarbonyl or aryl;

and in which furthermore
R$^4$ represents the radical —X—R$^8$,
wherein
X represents oxygen, sulphur, —SO— or —SO$_2$, and
R$^8$ represents an optionally substituted radical from the series comprising C$_1$–C$_6$-alkyl, alkenyl, alkinyl, cycloalkyl, phenylalkyl and aryl,
and in which furthermore
R$^4$ represents the radical

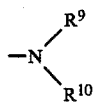

wherein
R$^9$ represents hydrogen or optionally substituted alkyl and
R$^{10}$ represents an optionally substituted radical from the series comprising alkyl, alkenyl, alkinyl, cycloalkyl, aralkyl, aryl, heteroaryl, alkyl- or alkoxycarbonyl and alkyl- or arylsulphonyl, or
R$^9$ and R$^{10}$ together represent alkanediyl which is optionally interrupted by an oxygen atom;
and in which furthermore
R$^4$ represents the radical

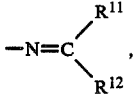

wherein
R$^{11}$ represents hydrogen or optionally substituted alkyl and
R$^{12}$ represents an optionally substituted radical from the series comprising alkyl, alkenyl, alkinyl, cycloalkyl, aralkyl and aryl or
R$^{11}$ and R$^{12}$ together represent alkanediyl,
and in which furthermore
R$^4$ represents trialkylsilyl or the radical

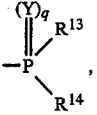

wherein
q represents the numbers zero or 1,
Y represents oxygen or sulphur and
R$^{13}$ and R$^{14}$ are identical or different and individually represent optionally substituted radicals from the series comprising alkyl, alkenyl, aralkyl, alkinyl, aryl, alkoxy, alkenoxy, alkinoxy, aralkoxy, aryloxy, alkylthio, alkenylthio, aralkylthio, alkinylthio, arylthio, amino, alkylamino and dialkylamino, or
R$^{13}$ and R$^{14}$ together represent alkanedioxy, oxyalkyleneamino or alkanediamino;
and in which furthermore
R$^4$ represents an optionally substituted heterocyclic radical,
and in which furthermore
M represents hydrogen, one equivalent of a metal, or an ammonium radical which is optionally substituted by alkyl, alkenyl, alkinyl and/or aralkyl, or—in the case in which M is bonded to the same nitrogen atom as $R^2$—also represents an optionally substituted radical from the series comprising alkyl, alkenyl, alkinyl and aralkyl.

Furthermore, new 1:1 adducts of compounds of the formula (I), wherein, in this case, M represents hydrogen and $R^1$, $R^2$, $R^3$ and $R^4$ have the meanings given above, with strong acids have been found.

In the case in which M represents hydrogen, the new guanidine derivatives illustrated by the general formula (I) occur as mixtures of tautomers of the formulae (IA) and (IB):

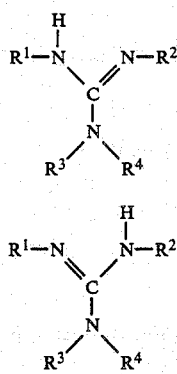

(IA)

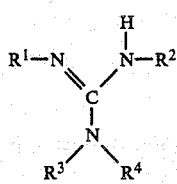

(IB)

The ratio in the mixture depends on aggregation-determining factors, such as, for example, temperature, solvent and concentration.

In the case in which, in addition to M, $R^3$ and/or $R^4$ also represent hydrogen, the general formula (I) also represents other possible tautomers, as illustrated in the formulae (IC) and (ID):

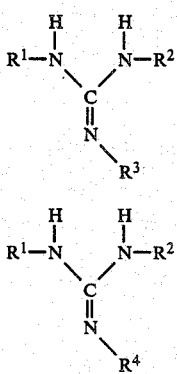

(IC)

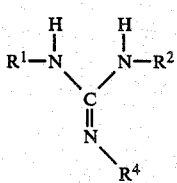

(ID)

The new guanidine derivatives of the formula (I) are obtained (a) in the case in which $R^1$ represents hydrogen, $R^3$ represents hydrogen or an optionally substituted radical from the series comprising alkyl, cycloalkyl, alkenyl, alkinyl and aralkyl, M represents hydrogen or an optionally substituted radical from the series comprising alkyl, alkenyl, alkinyl and aralkyl, and the radicals $R^2$ and $R^4$ have the meanings given above, if cyano compounds of the formula (II)

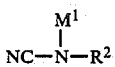

(II)

in which $M^1$ represents hydrogen or an optionally substituted radical from the series comprising alkyl, alkenyl, alkinyl and aralkyl and $R^2$ has the meaning given above, are reacted with amino compounds of the formula (III)

(III)

in which $R^3$ represents hydrogen or an optionally substituted radical from the series comprising alkyl, cycloalkyl, alkenyl, alkinyl and aralkyl, and $R^4$ has the meaning given above, or with hydrochlorides of amino compounds of the formula (III), if appropriate in the presence of diluents, and, if required, the reaction products are treated with acid acceptors; or (b) in the case in which $R^1$ represents the radical $-S(O)_m-R^5$, wherein m and $R^5$ have the meanings given above, and M represents hydrogen or an optionally substituted radical from the series comprising alkyl, alkenyl alkinyl and aralkyl, and wherein furthermore the radicals $R^2$, $R^3$ and $R^4$ have the meanings given above, or in the case in which $R^3$ represents the radical $-S(O)_n-R^6$, wherein n and $R^6$ have the meanings given above, and M represents hydrogen or an optionally substituted radical from the series comprising alkyl, alkenyl, alkinyl and aralkyl, and wherein furthermore the radicals $R^1$, $R^2$ and $R^4$ have the meanings given above, if the guanidine derivatives of the formula (I) which are obtainable by the preparation process described above under (a) and in which $R^1$ represents hydrogen, $R^3$ represents hydrogen or an optionally substituted radical from the series comprising alkyl, cycloalkyl, alkenyl, alkinyl and aralkyl, M represents hydrogen or an optionally substituted radical from the series comprising alkyl, alkenyl, alkinyl and aralkyl, and the radicals $R^2$ and $R^4$ have the meanings given above, are reacted with halogen/sulphur compounds of the formula (IV)

(IV)

in which $X^1$ represents fluorine, chlorine or bromine and m and $R^5$ have the meanings given above, and/or with halogen/sulphur compounds of the formula (V)

(V)

in which $X^2$ represents fluorine, chlorine or bromine and n and $R^6$ have the meanings given above, if appropriate in the presence of acid acceptors and, if appropriate, in the presence of diluents; or (c) in the case in which $R^3$ represents hydrogen or an optionally substituted radical from the series comprising alkyl, cycloalkyl, alkenyl, alkinyl and aralkyl, and M and the radicals $R^1$, $R^2$ and $R^4$ have the meanings given above, if isothioureas of the formula (VI)

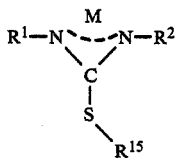 (VI)

in which
$R^{15}$ represents optionally substituted alkyl or aralkyl and
M and the radicals $R^1$ and $R^2$ have the meanings given above,
are reacted with amino compounds of the formula (III)

 (III)

in which
$R^3$ represents hydrogen or an optionally substituted radical from the series comprising alkyl, cycloalkyl, alkenyl, alkinyl and aralkyl and
$R^4$ has the meaning given above,
or with hydrochlorides of amino compounds of the formula (III), if appropriate in the presence of acid acceptors and, if appropriate, in the presence of diluents, and, if required, the reaction products are treated with acids; or (d) in the case in which $R^3$ represents hydrogen or an optionally substituted radical from the series comprising alkyl, cycloalkyl, alkenyl, alkinyl and aralkyl, and M and the radicals $R^1$, $R^2$ and $R^4$ have the meanings given above, if guanidine derivatives of the formula (I) in which
$R^3$ represents the radical $-S(O)_n-R^6$, wherein n and $R^6$ have the meanings given above, and
M and the radicals $R^1$, $R^2$ and $R^4$ have the meanings given above,
are reacted with amino compounds of the formula (III)

 (III)

in which
$R^3$ represents hydrogen or an optionally substituted radical from the series comprising alkyl, cycloalkyl, alkenyl, alkinyl and aralkyl, and
$R^4$ has the meaning given above,
or with hydrochlorides of amino compounds of the formula (III), if appropriate in the presence of acid acceptors and, if appropriate, in the presence of diluents; or (e) in the case in which M represents one equivalent of a metal or represents an ammmonium radical which is optionally substituted by alkyl, alkenyl, alkinyl and/or aralkyl, and the radicals $R^1$, $R^2$, $R^3$ and $R^4$ have the meanings given above, if guanidine derivatives of the formula (I) in which
M represents hydrogen, and
the radicals $R^1$, $R^2$, $R^3$ and $R^4$ have the meanings given above,
are reacted with metal hydroxides, hydrides or alkanolates or with organometallic compounds or with ammonia or appropriate amines, if appropriate in the presence of diluents; or (f) in the case in which 1:1 adducts of guanidine derivatives of the formula (I) with strong acids are to be prepared, if guanidine derivatives of the formula (I) in which
M and the radicals $R^1$, $R^2$, $R^3$ and $R^4$ have the meanings given above,
are reacted with strong acids, if appropriate using inert diluents.

The new guanidine derivatives of the formula (I) and their 1:1 adducts with strong acids are distinguished by powerful herbicidal activity and/or are suitable for regulating the growth of certain plants.

Surprisingly, the new compounds of the formula (I) have a substantially better herbicidal and plant growth-regulating action than previously known guanidines having the same direction of action, and exhibit good selectivity in cotton and in various species of cereal.

The invention preferably relates to compounds of the formula (I) in which
$R^1$ represents hydrogen or the radical $-S(O)_m-R^5$, wherein
m represents the numbers zero, 1 or 2 and
$R^5$ represents alkyl having up to 6 carbon atoms which is optionally substituted by halogen [such as, in particular, fluorine, chlorine and/or bromine], and wherein furthermore
$R^5$ represents the radical

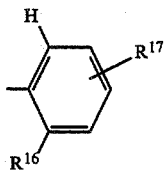

wherein
$R^{16}$ and $R^{17}$ are identical or different and represent hydrogen, halogen [such as, in particular, fluorine, chlorine and/or bromine], cyano, nitro, $C_1$-$C_6$-alkyl [which is optionally substituted by fluorine, chlorine, bromine, cyano, carboxyl, $C_1$-$C_4$-alkoxycarbonyl, $C_1$-$C_4$-alkylaminocarbonyl, di-($C_1$-$C_4$-alkyl)-aminocarbonyl, hydroxyl, $C_1$-$C_4$-alkoxy, formyloxy, $C_1$-$C_4$-alkyl-carbonyloxy, $C_1$-$C_4$-alkoxy-carbonyloxy, $C_1$-$C_4$-alkylamino-carbonyloxy, $C_1$-$C_4$-alkylthio, $C_1$-$C_4$-alkylsulphinyl, $C_1$-$C_4$-alkylsulphonyl, di-($C_1$-$C_4$-alkyl)-aminosulphonyl, $C_3$-$C_6$-cycloalkyl or phenyl], $C_2$-$C_6$-alkenyl [which is optionally substituted by fluorine, chlorine, bromine, cyano, $C_1$-$C_4$-alkoxy-carbonyl, carboxyl or phenyl], $C_1$-$C_4$-alkoxy [which is optionally substituted by fluorine, chlorine, bromine, cyano, carboxyl, $C_1$-$C_4$-alkoxy-carbonyl, $C_1$-$C_4$-alkylthio, $C_1$-$C_4$-alkylsulphinyl or $C_1$-$C_4$-alkylsulphonyl], $C_3$-$C_6$-alkenoxy [which is optionally substituted by fluorine, chlorine, bromine, cyano or $C_1$-$C_4$-alkoxy-carbonyl], $C_3$-$C_6$-alkinoxy or the radical $-S(O)_p-R^{18}$, wherein p represents the numbers zero, 1 or 2 and $R^{18}$ represents $C_1$-$C_4$-alkyl [which is optionally substituted by fluorine, chlorine, bromine, cyano or $C_1$-$C_4$-alkoxycarbonyl], C$_3$-C$_6$-alkenyl, C$_3$-C$_6$-alkinyl, C$_1$-C$_4$-alkoxy, C$_1$-C$_4$-alkylamino or di-(C$_1$-C$_4$-alkyl)-amino, or represents phenyl or phenoxy, C$_1$-C$_4$-alkyl-carbonylamino, C$_1$-C$_4$-alkoxy-carbonylamino, C$_1$-C$_4$-alkylamino-carbonylamino, di-(C$_1$-C$_4$-alkyl)-amino-carbonylamino or the radical —CO—R$^{19}$, wherein R$^{19}$ represents C$_1$-C$_6$-alkyl, C$_1$-C$_6$-alkoxy, C$_3$-C$_6$-alkenoxy, C$_1$-C$_4$-alkylthio, C$_1$-C$_4$-alkylamino or di-(C$_1$-C$_4$-alkyl)-amino [which is optionally substituted by fluorine and/or chlorine], or represents C$_1$-C$_4$-alkylsulphonyloxy, di-(C$_1$-C$_4$-alkyl)-aminosulphonylamino or the radical —CH=N—R$^{20}$, wherein R$^{20}$ represents C$_1$-C$_6$-alkyl which is optionally substituted by fluorine, chlorine, cyano, carboxyl, C$_1$-C$_4$-alkoxy-carbonyl, C$_1$-C$_4$-alkylthio, C$_1$-C$_4$-alkylsulfinyl, or C$_1$-C$_4$-alkylsulphonyl, benzyl which is optionally substituted by fluorine or chlorine, C$_3$-C$_6$-alkenyl or C$_3$-C$_6$-alkinyl which is optionally substituted by fluorine or chlorine, phenyl which is optionally substituted by fluorine, chlorine, bromine, C$_1$-C$_4$-alkyl, C$_1$-C$_4$-alkoxy, trifluoromethyl, trifluoromethoxy or trifluoromethylthio, C$_3$-C$_6$-alkenoxy, C$_3$-C$_6$-alkinoxy, benzyloxy or C$_1$-C$_6$-alkoxy which is optionally substituted by fluorine and/or chlorine, or represents amino, C$_1$-C$_4$-alkylamino, di-(C$_1$-C$_4$-alkyl)-amino, phenylamino, C$_1$-C$_4$-alkyl-carbonylamino, C$_1$-C$_4$-alkoxycarbonylamino or C$_1$-C$_4$-alkyl-sulphonylamino, or represents phenylsulphonylamino which is optionally substituted by fluorine, chlorine, bromine or methyl;

and wherein furthermore
R$^5$ represents the radical

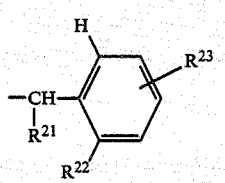

wherein
R$^{21}$ represents hydrogen or C$_1$-C$_3$-alkyl and
R$^{22}$ and R$^{23}$ are identical or different and represent hydrogen, fluorine, chlorine, bromine, nitro, cyano, C$_1$-C$_4$-alkyl [which is optionally substituted by fluorine and/or chlorine], C$_1$-C$_4$-alkoxy [which is optionally substituted by fluorine and/or chlorine], carboxyl, C$_1$-C$_4$-alkoxycarbonyl, C$_1$-C$_4$-alkylsulphonyl or di-(C$_1$-C$_4$-alkyl)-aminosulphonyl;

and wherein furthermore
R$^5$ represents the radical

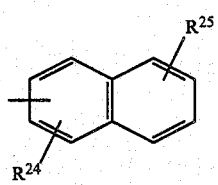

wherein
R$^{24}$ and R$^{25}$ are identical or different and represent hydrogen, fluorine, chlorine, bromine, nitro, cyano, C$_1$-C$_4$-alkyl [which is optionally substituted by fluorine and/or chlorine] or C$_1$-C$_4$-alkoxy [which is optionally substituted by fluorine and/or chlorine];

and wherein furthermore
R$^5$ represents the radical

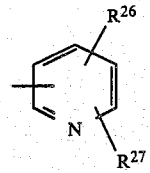

wherein
R$^{26}$ and R$^{27}$ are identical or different and represent hydrogen, fluorine, chlorine, bromine, nitro, cyano, C$_1$-C$_4$-alkyl [which is optionally substituted by fluorine and/or chlorine], C$_1$-C$_4$-alkoxy [which is optionally substituted by fluorine and/or chlorine], C$_1$-C$_4$-alkylthio, C$_1$-C$_4$-alkylsulphinyl or C$_1$-C$_4$-alkylsulphonyl [which are optionally substituted by fluorine and/or chlorine], and di-(C$_1$-C$_4$-alkyl)-aminosulphonyl or C$_1$-C$_4$-alkoxy-carbonyl, and wherein furthermore
R$^5$ represents the radical

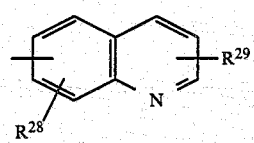

wherein
R$^{28}$ and R$^{29}$ are identical or different and represent hydrogen, fluorine, chlorine, bromine, C$_1$-C$_4$-alkyl [which is optionally substituted by fluorine and/or bromine], C$_1$-C$_4$-alkoxy [which is optionally substituted by fluorine and/or chlorine], C$_1$-C$_4$-alkylthio, C$_1$-C$_4$-alkylsulphinyl or C$_1$-C$_4$-alkylsulphonyl [which are optionally substituted by fluorine and/or chlorine] or di-(C$_1$-C$_4$-alkyl)-aminosulphonyl, and wherein furthermore
R$^5$ represents the radical

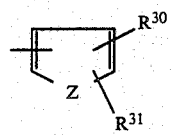

wherein
R$^{30}$ and R$^{31}$ are identical or different and represent hydrogen, fluorine, chlorine, bromine, cyano, nitro, C$_1$-C$_4$-alkyl [which is optionally substituted by fluorine and/or chlorine], C$_1$-C$_4$-alkoxy [which is optionally substituted by fluorine and/or chlorine], C$_1$-C$_4$-alkylthio, C$_1$-C$_4$-alkylsulphinyl or C$_1$-C$_4$-alkylsulphonyl [which is optionally substituted by fluorine and/or chlorine], di-(C$_1$-C$_4$-alkyl)-aminosulphonyl or C$_1$-C$_4$-alkoxy-carbonyl, and
Z represents oxygen, sulphur or the grouping N—Z$^1$,
wherein
Z$^1$ represents hydrogen, C$_1$-C$_4$-alkyl [which is optionally substituted by fluorine, chlorine, bromine or cyano], C$_3$-C$_6$-cycloalkyl, benzyl, phenyl

[which is optionally substituted by fluorine, chlorine, bromine or nitro], C$_1$–C$_4$-alkyl-carbonyl, C$_1$–C$_4$-alkoxy-carbonyl or di-(C$_1$–C$_4$-alkyl)-aminocarbonyl, and in which furthermore
R$^2$ represents the radical

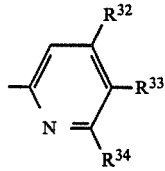

wherein
R$^{32}$ and R$^{34}$ are identical or different and represent hydrogen, fluorine, chlorine, bromine, C$_1$–C$_4$-alkyl [which is optionally substituted by fluorine and/or chlorine] or C$_1$–C$_4$-alkoxy [which is optionally substituted by fluorine and/or chlorine], with the proviso that at least one of the radicals R$^{32}$ and R$^{34}$ is not hydrogen, and R$^{33}$ represents hydrogen, fluorine, chlorine, bromine, cyano or C$_1$–C$_4$-alkyl [which is optionally substituted by fluorine and/or chlorine];

and in which furthermore
R$^2$ represents the radical

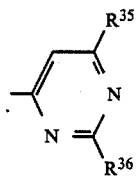

wherein
R$^{35}$ and R$^{36}$ are identical or different and represent hydrogen, fluorine, chlorine, bromine, C$_1$–C$_4$-alkyl [which is optionally substituted by fluorine and/or chlorine], C$_1$–C$_4$-alkoxy [which is optionally substituted by fluorine and/or chlorine], C$_1$–C$_4$-alkylamino or di-(C$_1$–C$_4$-alkyl)-amino, with the proviso that at least one of the radicals R$^{35}$ and R$^{36}$ is not hydrogen;

and in which furthermore
R$^2$ represents the radical

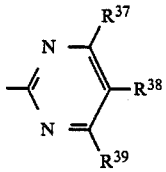

wherein
R$^{37}$ represents hydrogen, fluorine, chlorine, bromine, C$_1$–C$_4$-alkyl [which is optionally substituted by fluorine and/or chlorine] or C$_1$–C$_4$-alkoxy [which is optionally substituted by fluorine and/or chlorine], R$^{38}$ represents hydrogen, fluorine, chlorine, bromine, C$_1$–C$_4$-alkyl [which is optionally substituted by fluorine and/or chlorine], cyano, formyl, C$_1$–C$_4$-alkyl-carbonyl or C$_1$–C$_4$-alkoxycarbonyl, and R$^{39}$ represents C$_1$–C$_4$-alkyl [which is optionally substituted by fluorine and/or chlorine], C$_1$–C$_4$-alkoxy [which is optionally substituted by fluorine and/or chlorine], amino, C$_1$–C$_4$-alkylamino or di-(C$_1$–C$_4$-alkyl)-amino, or R$^{38}$ and R$^{39}$ together represent C$_3$–C$_4$-alkanediyl, and in which furthermore
R$^2$ represents the radical

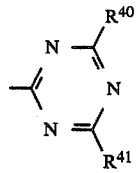

wherein
R$^{40}$ and R$^{41}$ are identical or different and represent C$_1$–C$_4$-alkyl [which is optionally substituted by fluorine and/or chlorine] or C$_1$–C$_4$-alkoxy [which is optionally substituted by fluorine and/or chlorine];

and in which furthermore
R$^3$ represents hydrogen, C$_1$–C$_4$-alkyl [which is optionally substituted by fluorine, chlorine, bromine, cyano, hydroxyl or C$_1$–C$_2$-alkoxy], C$_3$–C$_6$-cycloalkyl, C$_3$–C$_6$-alkenyl, C$_3$–C$_6$-alkinyl, benzyl [which is optionally substituted by fluorine, chlorine or methyl] or the radical —S(O)$_n$—R$^6$, wherein
n represents the numbers zero, 1 or 2 and
R$^6$ has the preferred meaning given above for R$^5$, but is not identical to R$^5$ in each individual case;

and in which furthermore
R$^4$ represents hydrogen or hydroxyl, with the proviso that then at least one of the radicals R$^1$ and R$^3$ is not hydrogen;

and in which furthermore
—in the case in which R$^3$ is not hydrogen—R$^4$ represents C$_1$–C$_6$-alkyl [which is optionally substituted by fluorine, chlorine, bromine, cyano, carboxyl, C$_1$–C$_4$-alkoxy-carbonyl, hydroxyl or C$_1$–C$_4$-alkoxy], C$_3$–C$_6$-cycloalkyl [which is optionally interrupted by a —SO$_2$— bridge], C$_3$–C$_6$-alkenyl, C$_3$–C$_6$-alkinyl, benzyl or phenylethyl [which is optionally substituted by fluorine, chlorine and/or methyl] or phenyl [which is optionally substituted by fluorine, chlorine, bromine, hydroxyl, cyano, nitro, amino, C$_1$–C$_4$-alkyl, trifluoromethyl, C$_1$–C$_4$-alkoxy, trifluoromethoxy, C$_1$–C$_4$-alkylthio, trifluoromethylthio, aminosulphonyl or C$_1$–C$_4$-alkoxycarbonyl], or R$^3$ and R$^4$ together represent C$_4$–C$_6$-alkanediyl which is optionally interrupted by an oxygen bridge or by a bridge >N—R$^7$, wherein
R$^7$ represents C$_1$–C$_4$-alkyl, C$_1$–C$_4$-alkylcarbonyl or phenyl [which is optionally substituted by fluorine, chlorine, bromine, cyano, nitro, C$_1$–C$_4$-alkyl, trifluoromethyl or C$_1$–C$_4$-alkoxy];

and in which furthermore
R$^4$ represents the radical —X—R$^8$, wherein
X represents oxygen, sulphur, —SO— or —SO$_2$— and
R$^8$ represents C$_1$–C$_6$-alkyl [which is optionally substituted by fluorine, chlorine, C$_1$–C$_4$-alkoxy, C$_1$–C$_4$-alkylthio, C$_1$–C$_4$-alkylsulphinyl or C$_1$–C$_4$-alkylsulphonyl], C<sub>3</sub>-C<sub>6</sub>-alkenyl, C<sub>3</sub>-C<sub>6</sub>-alkinyl, C<sub>3</sub>-C<sub>6</sub>-cycloalkyl, benzyl [which is optionally substituted by fluorine, chlorine or methyl] or phenyl [which is optionally substituted by fluorine, chlorine, bromine, nitro, cyano, $C_1$-$C_4$-alkyl, trifluoromethyl, $C_1$-$C_4$-alkoxy, trifluoromethoxy, $C_1$-$C_4$-alkylthio or trifluoromethylthio];
and in which furthermore
$R^4$ represents the radical

wherein
$R^9$ represents hydrogen or $C_1$-$C_4$-alkyl and
$R^{10}$ represents $C_1$-$C_4$-alkyl [which is optionally substituted by fluorine, chlorine, bromine, cyano, $C_1$-$C_4$-alkoxy or $C_1$-$C_4$-alkoxy-carbonyl], $C_3$-$C_6$-alkenyl, $C_3$-$C_6$-alkinyl, $C_3$-$C_6$-cycloalkyl [which is optionally interrupted by a —SO<sub>2</sub> bridge], benzyl or phenylethyl [which are optionally substituted by fluorine, chlorine or methyl], phenyl [which is optionally substituted by fluorine, chlorine, bromine, nitro, cyano, $C_1$-$C_4$-alkyl, trifluoromethyl, $C_1$-$C_4$-alkoxy, fluoromethoxy, $C_1$-$C_4$-alkylthio or trifluoromethylthio], pyrimidyl, $C_1$-$C_4$-alkyl-carbonyl, benzoyl, $C_1$-$C_4$-alkoxy-carbonyl, $C_1$-$C_4$-alkylsulphonyl or phenylsulphonyl [which is optionally substituted by fluorine, chlorine, bromine or methyl] or
$R^9$ and $R^{10}$ together represent $C_4$-$C_6$-alkanediyl [which is optionally interrupted by an oxygen bridge];
and in which furthermore
$R^4$ represents the radical

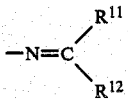

wherein
$R^{11}$ represents hydrogen or $C_1$-$C_4$-alkyl and
$R^{12}$ represents $C_1$-$C_4$-alkyl, $C_3$-$C_6$-alkenyl, $C_3$-$C_6$-alkinyl, $C_3$-$C_6$-cycloalkyl, benzyl or phenylethyl [which are optionally substituted by fluorine, chlorine or methyl] or phenyl [which is optionally substituted by fluorine, chlorine, bromine, $C_1$-$C_4$-alkyl, trifluoromethyl, cyano, nitro, $C_1$-$C_4$-alkoxy or trifluoromethoxy], or
$R^{11}$ and $R^{12}$ together represent $C_4$-$C_6$-alkanediyl;
and in which furthermore
$R^4$ represents tri-($C_1$-$C_4$-alkyl)-silyl or the radical

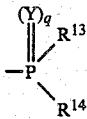

wherein
q represents the numbers zero or 1,
Y represents oxygen or sulphur and
$R^{13}$ and $R^{14}$ are identical or different and individually represent $C_1$-$C_4$-alkyl [which is optionally substituted by fluorine, chlorine, cyano or methoxy], $C_2$-$C_4$-alkenyl, $C_3$-$C_4$-alkinyl, benzyl [which is optionally substituted by fluorine, chlorine or methyl], phenyl [which is optionally substituted by fluorine, chlorine or methyl], $C_1$-$C_4$-alkoxy [which is optionally substituted by fluorine, chlorine, cyano or methoxy], $C_2$-$C_4$-alkenoxy, $C_3$-$C_4$-alkinoxy, benzyloxy [which is optionally substituted by fluorine, chlorine and/or methyl], phenoxy [which is optionally substituted by fluorine, chlorine, bromine, cyano, nitro, methyl, trifluoromethyl or methoxy], $C_1$-$C_4$-alkylthio [which is optionally substituted by fluorine, chlorine, cyano or methoxy], $C_2$-$C_4$-alkenylthio, benzylthio [which is optionally substituted by fluorine, chlorine or methyl], $C_3$-$C_4$-alkinylthio, phenylthio [which is optionally substituted by fluorine, chlorine, bromine, cyano, nitro, methyl, trifluoromethyl or methoxy], amino, $C_1$-$C_4$-alkylamino or di-($C_1$-$C_4$-alkyl)-amino, or together represent $C_2$-$C_5$-alkanedioxy, oxy-$C_1$-$C_3$-alkylamino or $C_1$-$C_3$-alkanediamino;
and in which furthermore
$R^4$ represents a five-membered or six-membered heterocyclic structure which contains 1 to 3 nitrogen atoms and/or an oxygen or sulphur atom and is optionally substituted by fluorine, chlorine, bromine, $C_1$-$C_4$-alkyl, trifluoromethyl, nitro, cyano or $C_1$-$C_4$-alkoxy;
and in which furthermore
M represents hydrogen, one equivalent of sodium, potassium, magnesium, calcium, aluminium, manganese, iron, cobalt or nickel, an ammonium radical which is optionally substituted by $C_1$-$C_6$-alkyl [which is optionally substituted by chlorine], $C_3$-$C_6$-alkenyl, $C_3$-$C_6$-alkinyl and/or benzyl [which is optionally substituted by fluorine, chlorine or methyl], or—in the case in which M is bonded to the same nitrogen atom as $R^2$—also represents $C_1$-$C_6$-alkyl [which is optionally substituted by fluorine, chlorine or cyano], $C_3$-$C_6$-alkenyl, $C_3$-$C_6$-alkinyl or benzyl.

The invention furthermore preferably relates to 1:1 adducts of compounds of the formula (I)—as defined above—with hydrohalic acids, such as hydrogen fluoride, chloride, bromide and iodide, with sulphuric acid, phosphoric acid, with alkanesulhonic acids which have up to 4 carbon atoms and are optionally substituted by fluorine or chlorine, or benzene- or naphthalenesulphonic acids which are optionally substituted by fluorine, chlorine or methyl.

The invention relates in particular to compounds of the formula (I) in which
(A) $R^1$ represents the radical —S(O)<sub>m</sub>—$R^5$,
wherein
m represents the number 2 and
$R^5$ represents the radical

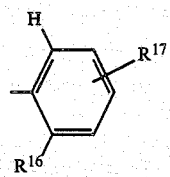

wherein

R[16] represents fluorine, chlorine, bromine, methyl, trifluoromethyl, C$_1$-C$_2$-alkoxy, difluoromethoxy, trifluoromethoxy, phenyl or C$_1$-C$_2$-alkoxycarbonyl and R[17] represents hydrogen;

and in which furthermore

R[2] represents the radical

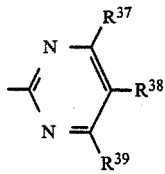

wherein

R[37] represents hydrogen, methyl or methoxy,

R[38] represents hydrogen, chlorine, methyl, acetyl or methoxycarbonyl and

R[39] represents C$_1$-C$_4$-alkyl or C$_1$-C$_4$-alkoxy or, together with R[38], represents C$_3$-C$_4$-alkanediyl;

and in which furthermore

R[3] represents hydrogen, methyl or the radical —S(O)$_n$—R[6], n represents the number 2 and R[6] has the particularly preferred meaning given above for R[5];

and in which furthermore

R[4] represents hydroxyl, C$_1$-C$_4$-alkoxy, C$_3$-C$_4$-alkenoxy, C$_3$-C$_4$-alkinoxy, benzyloxy or the radical

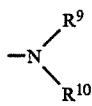

wherein

R[9] represents hydrogen or methyl and

R[10] represents C$_1$-C$_3$-alkyl, phenyl, acetyl, methoxycarbonyl, phenylsulphonyl or p-toluenesulphonyl;

and in which furthermore

M represents hydrogen, sodium, potassium or one equivalent of magnesium or calcium; and—in the case in which M represents hydrogen—the 1:1 adducts of the compounds defined above with hydrochloric acid, sulphuric acid, benzenesulphonic acid and p-toluenesulphonic acid;

or in which (B) R[1] represents hydrogen or the radical —S(O)$_m$—R[5], m represents the numbers zero, 1 or 2 and R[5] represents the radical

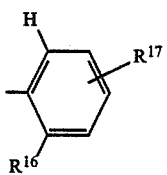

wherein

R[16] and R[17] represent hydrogen or

R[16] represents chlorine, nitro, methyl, trifluoromethyl or methoxy and

R[17] represents fluorine, chlorine, bromine, methyl, trifluoromethyl, cyano, nitro or methoxy;

and in which furthermore

R[2] represents the radical

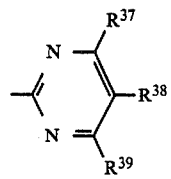

wherein

R[37] represents hydrogen, methyl or methoxy,

R[38] represents hydrogen, chlorine, methyl, acetyl or methoxycarbonyl and

R[39] represents C$_1$-C$_4$-alkyl or C$_1$-C$_4$-alkoxy or

R[38] and R[39] together represent C$_3$-C$_4$-alkanediyl, and in which furthermore R[3] represents hydrogen, methyl or the radical —S(O)$_n$—R[6], wherein n represents the numbers zero, 1 or 2 and R[6] has the particularly preferred meaning given above for R[5];

and in which furthermore

R[4] represents hydroxyl, with the proviso that then at least one of the radicals R[1] and R[3] is not hydrogen;

and in which furthermore

R[4] represents C$_1$-C$_4$-alkoxy, C$_3$-C$_4$-alkenoxy, C$_3$-C$_4$-alkinoxy, benzoyloxy or the radical

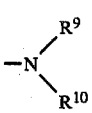

wherein

R[9] represents hydrogen or methyl and

R[10] represents C$_1$-C$_3$-alkyl, phenyl, acetyl, methoxycarbonyl, phenylsulphonyl or p-toluenesulphonyl;

and in which furthermore

M represents hydrogen, sodium, potassium or one equivalent of magnesium or calcium, and—in the case in which M represents hydrogen—the 1:1 adducts of the compounds defined above with hydrochloric acid, sulphuric acid, benzenesulphonic acid and p-toluenesulphonic acid;

or in which (C) R[1] represents hydrogen or the radical —S(O)$_m$—R[5], wherein m represents the numbers zero, 1 or 2 and R[5] represents the radical

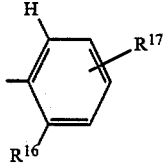

wherein

R[16] represents hydrogen, fluorine, chlorine, bromine, nitro, methyl, trifluoromethyl, C$_1$-C$_2$-alkoxy, difluoromethoxy, trifluoromethoxy, phenyl or $C_1$-$C_2$-alkoxy-carbonyl and $R^{17}$ represents hydrogen, fluorine, chlorine, bromine, nitro, methyl, trifluoromethyl, $C_1$-$C_2$-alkoxy, difluoromethoxy or trifluoromethoxy, and in which furthermore $R^2$ represents the radical

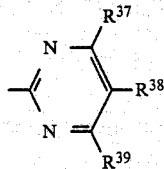

wherein $R^{37}$ represents hydrogen, methyl or methoxy, $R^{38}$ represents hydrogen, chlorine, methyl, acetyl or methoxycarbonyl and $R^{39}$ represents $C_1$-$C_4$-alkyl or $C_1$-$C_4$-alkoxy or $R^{38}$ and $R^{39}$ together represent $C_3$-$C_4$-alkanediyl, and in which furthermore $R^3$ represents hydrogen, with the proviso that then $R^1$ is not hydrogen, or represents optionally hydroxyl-substituted $C_1$-$C_4$-alkyl, or $C_5$-$C_6$-cycloalkyl, $C_3$-$C_4$-alkenyl or $C_3$-$C_4$-alkinyl; benzyl or the radical —S(O)$_n$—R$^6$, wherein n represents the numbers zero, 1 or 2 and $R^6$ has the particularly preferred meaning given above for $R^5$;

and in which furthermore $R^4$ represents $C_1$-$C_4$-alkyl which is optionally substituted by chlorine, cyano, $C_1$-$C_3$-alkoxy-carbonyl, hydroxyl or $C_1$-$C_2$-alkoxy, or represents $C_3$-$C_6$-cycloalkyl, $C_3$-$C_4$-alkenyl, $C_3$-$C_4$-alkinyl or benzyl, or represents phenyl which is optionally substituted by fluorine, chlorine, bromine, nitro, cyano, aminosulphonyl, hydroxyl, amino, methyl, trifluoromethyl, methoxy, trifluoromethoxy, methylthio, trifluoromethylthio or $C_1$-$C_2$-alkoxy-carbonyl, or—in the case in which $R^1$ is not hydrogen—also represents hydrogen;

and in which furthermore

M represents hydrogen, sodium, or potassium or one equivalent of magnesium or calcium, or $C_1$-$C_4$-alkyl-, di-($C_1$-$C_4$-alkyl)- or tri-($C_1$-$C_4$-alkyl)-ammonium;

and—in the case in which M represents hydrogen—the 1:1 adducts of the compounds defined above with hydrochloric acid, sulphuric acid, benzenesulphonic acid and p-toluenesulphonic acid;

or in which (D) $R^1$ represents the radical —S(O)$_m$—R$^5$, wherein m represents the number 2 and $R^5$ represents the radical

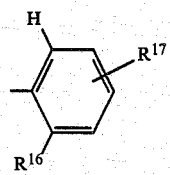

wherein $R^{16}$ represents fluorine, chlorine, bromine, methyl, trifluoromethyl, $C_1$-$C_2$-alkoxy, difluoromethoxy, trifluoromethoxy or $C_1$-$C_2$-alkoxy-carbonyl and $R^{17}$ represents hydrogen;

and in which furthermore $R^2$ represents the radical

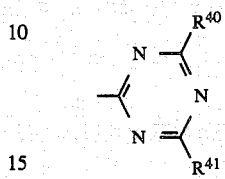

wherein $R^{40}$ represents methyl, methoxy or ethoxy and $R^{41}$ represents methyl, methoxy or ethoxy;

and in which furthermore $R^3$ represents hydrogen, methyl or the radical —S(O)$_n$—R$^6$, wherein n represents the number 2 and $R^6$ has the particularly preferred meaning given above for $R^5$;

and in which furthermore $R^4$ represents hydroxyl, $C_1$-$C_4$-alkoxy, $C_3$-$C_4$-alkenoxy, $C_3$-$C_4$-alkinoxy, benzyloxy o radical

wherein $R^9$ represents hydrogen or methyl and $R^{10}$ represents $C_1$-$C_3$-alkyl, phenyl, acetyl, methoxycarbonyl, phenylsulphonyl or p-toluenesulphonyl;

and in which furthermore

M represents hydrogen, sodium or potassium or one equivalent of magnesium or calcium; and—in the case in which M represents hydrogen—the 1:1 adducts of the compounds defined above with hydrochloric acid, sulphuric acid, benzenesulphonic acid and p-toluenesulphonic acid;

or in which (E) $R^1$ represents hydrogen or the radical —S(O)$_m$—R$^5$, m represents the numbers zero, 1 or 2 and $R^5$ represents the radical

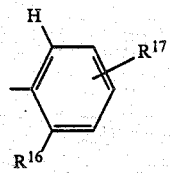

wherein $R^{16}$ and $R^{17}$ both represent hydrogen, or $R^{16}$ represents chlorine, nitro, methyl, trifluoromethyl or methoxy and $R^{17}$ represents fluorine, chlorine, bromine, methyl, trifluoromethyl, cyano, nitro or methoxy;

and in which furthermore $R^2$ represents the radical

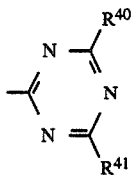

wherein
$R^{40}$ represents methyl, methoxy or ethoxy and
$R^{41}$ represents methyl, methoxy or ethoxy;
and in which furthermore
$R^3$ represents hydrogen, methyl or the radical —S-(O)$_n$—R$^6$,
n represents the numbers zero, 1 or 2 and
$R^6$ has the particularly preferred meaning given above for $R^5$;
and in which furthermore
$R^4$ represents hydroxyl, with the proviso that then at least one of the radicals $R^1$ and $R^3$ is not hydrogen;
and in which furthermore
$R^4$ represents $C_1$-$C_4$-alkoxy, $C_3$-$C_4$-alkenoxy, $C_3$-$C_4$-alkinoxy, benzyloxy or the radical

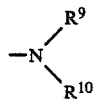

wherein
$R^9$ represents hydrogen or methyl and
$R^{10}$ represents $C_1$-$C_3$-alkyl, phenyl, acetyl, methoxycarbonyl, phenylsulphonyl or p-toluenesulphonyl;
and in which furthermore
M represents hydrogen, sodium or potassium or one equivalent of magnesium or calcium, and—in the case in which
M represents hydrogen—the 1:1 adducts of the compounds defined above with hydrochloric acid, sulphuric acid, benzenesulphonic acid and p-toluenesulphonic acid;
or in which (F) $R^1$ represents hydrogen or the radical —S(O)$_m$—R$^5$,
wherein
m represents the numbers zero, 1 or 2 and
$R^5$ represents the radical

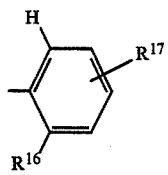

wherein
$R^{16}$ represents hydrogen, fluorine, chlorine, bromine, nitro, methyl, trifluoromethyl, $C_1$-$C_2$-alkoxy, difluoromethoxy, trifluoromethoxy or $C_1$-$C_2$-alkoxy and
$R^{17}$ represents hydrogen, fluorine, chlorine, bromine, nitro, methyl, trifluoromethyl, $C_1$-$C_2$-alkoxy, difluoromethoxy or trifluoromethoxy,
and in which furthermore
$R^2$ represents the radical

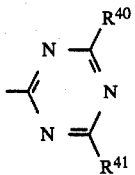

$R^{40}$ represents methyl, methoxy or ethoxy and
$R^{41}$ represents methyl, methoxy or ethoxy;
and in which furthermore
$R^3$ represents hydrogen, optionally hydroxyl-substituted $C_1$-$C_4$-alkyl, $C_5$-$C_6$-cycloalkyl, $C_3$-$C_4$-alkenyl, $C_3$-$C_4$-alkinyl, benzyl or the radical —S-(O)$_n$—R$^6$,
wherein
n represents the numbers zero, 1 or 2 and
$R^6$ has the particularly preferred meaning given above for $R^5$;
and in which furthermore
$R^4$ represents $C_1$-$C_4$-alkyl which is optionally substituted by chlorine, cyano, $C_1$-$C_3$-alkoxycarbonyl, hydroxyl or $C_1$-$C_2$-alkoxy, or represents $C_5$-$C_6$-cycloalkyl, $C_3$-$C_4$-alkenyl, $C_3$-$C_4$-alkinyl or benzyl, or represents phenyl which is optionally substituted by fluorine, chlorine, bromine, nitro, cyano, aminosulphonyl, hydroxyl, amino, methyl, trifluoromethyl, methoxy, trifluoromethoxy, methylthio, trifluoromethylthio or $C_1$-$C_2$-alkoxy-carbonyl, or—in the case in which at least one of the radicals $R^1$ and $R^3$ is not hydrogen—also represents hydrogen;
and in which furthermore
M represents hydrogen, sodium or potassium or one equivalent of magnesium or calcium, or $C_1$-$C_4$-alkyl-, di-($C_1$-$C_4$-alky)- or tri-($C_1$-$C_4$-alkyl)ammonium; and—in the case in which M represents hydrogen—the 1:1 adducts of the compounds defined above with hydrochloric acid, sulphuric acid, benzenesulphonic acid and p-toluenesulphonic acid.

If, for example, O-isopropyl-hydroxylamine hydrochloride and 2-cyanoamino-4-methoxy-6-methylpyrimidine are used as starting materials for process variant (a), the course of the reaction can be represented by the following equation:

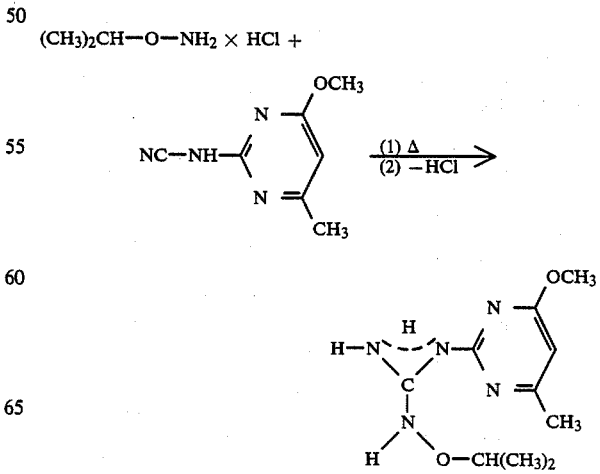

If, for example, 2-difluoromethoxy-benzenesulphonyl chloride and N'-(4-methoxy-6-methyl-s-triazin-2-yl)-N''-dimethylamino-guanidine are used as starting materials for process variant (b), the course of the reaction can be represented by the following equation:

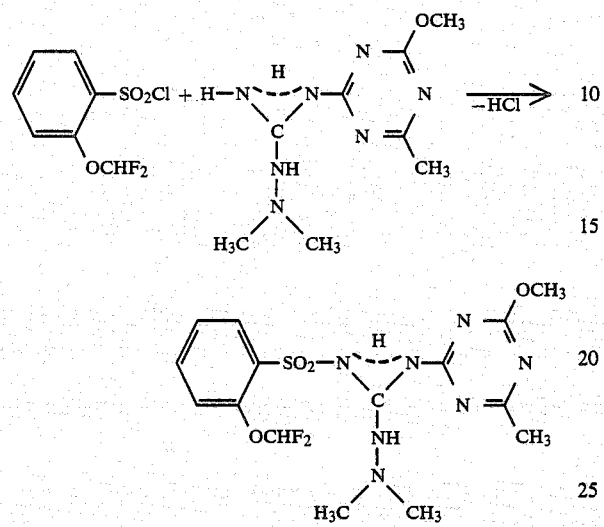

If for example, N'-(4-methoxy-6-methyl-pyrimidin-2-yl)-N'''-(2-fluorobenzenesulphonyl)-S-methyl-isothiourea and diethylamine are used as starting materials for process variant (c), and the ammonium salt initially obtained is treated with hydrochloric acid, the course of the reaction can be represented by the following equation:

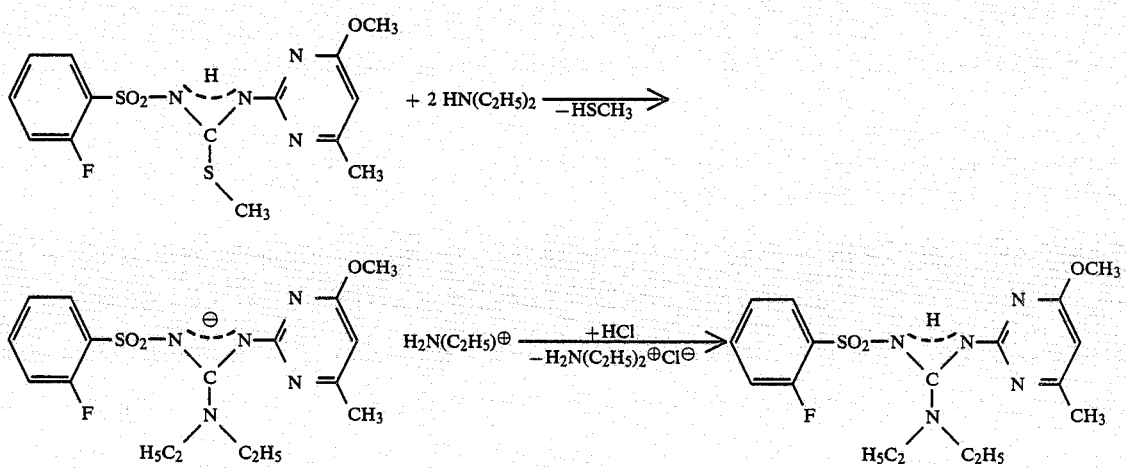

If, for example, N'-(4,6-dimethoxy-s-triazin-2-yl)-N''-methoxy-N'',N'''-bis-(2-trifluoromethyl-benzenesulphonyl)-guanidine and ammonia are used as starting materials for process variant (d), the course of the reaction can be represented by the following equation:

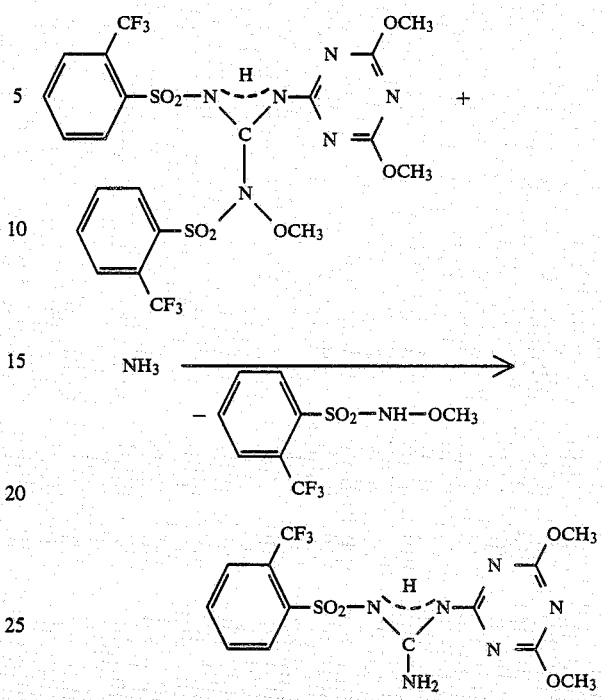

If, for example, N'-(4,6-dimethoxy-pyrimidin-2-yl)-N''-methoxy-N'''-(2-trifluoro-methoxy-benzenesulphonyl)-guanidine and potassium ethanolate are used as starting materials for process variant (e), the course of the reaction can be represented by the following equation:

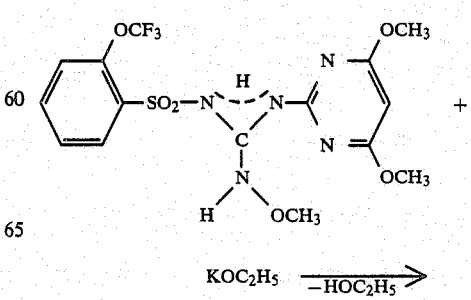

-continued

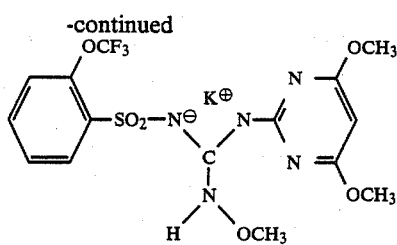

If, for example, N'-4,6-dimethyl-pyrimidin-2-yl)-N'''-methyl-N''''-(2-methoxycarbonyl-benzenesulphonyl)-guanidine and trifluoromethane-sulphonic acid are used as starting materials for process variant (f), the course of the reaction can be represented by the following equation:

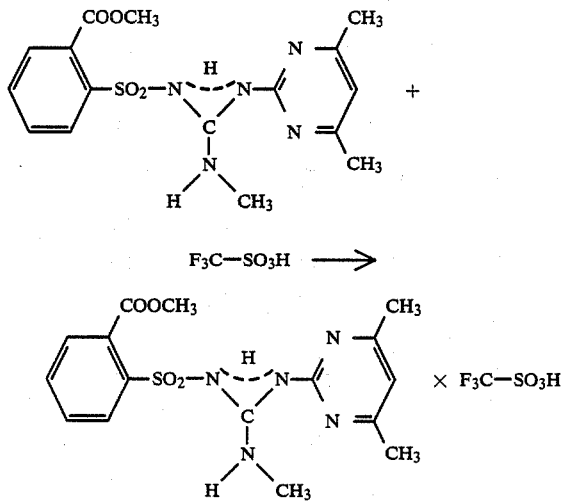

In accordance with a further aspect of the invention it has been found that when the starting material is of the formula

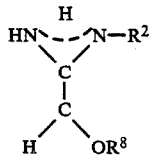

the reaction with

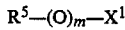

proceeds stepwise. If up to one mole of the sulphonylating agent is employed, the H on the nitrogen atom which carries the $OR^8$ moiety is selectively attacked to produce

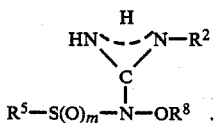

The next point of attack is the other NH radical but, surprisingly, only one additional $R^5—S(O)_m$—radical is added even if an excess is employed, not two additional radicals as would have been expected, i.e. even if more than two moles of the sulphonylating agent are employed the product is disulphonylated selectively but not tri-sulphonylated, viz.

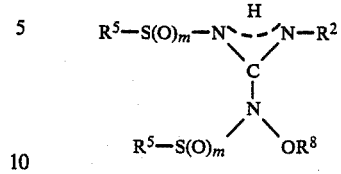

By contrast, similar sulphonylations of urea derivatives result in dehydration, e.g.

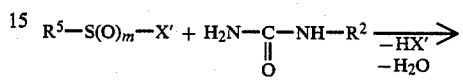

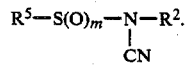

Formula (II) gives a general definition of the cyano compounds to be used as starting materials for process variant (a). In this formula, $M^1$ preferably represents hydrogen, $C_1$–$C_6$-alkyl [which is optionally substituted by fluorine, chlorine or cyano], $C_3$–$C_6$-alkenyl, $C_3$–$C_6$-alkinyl or benzyl, in particular hydrogen, and $R^2$ preferably or particularly has the same meaning as given above within the framework of the definition of substituents for formula (I) as being preferred or particularly preferred respectively.

The following may be mentioned as examples of starting materials of the formula (II): 2-cyanoamino-4,6-dimethyl-pyrimidine, 2-cyanoamino-4-methoxy-6-methyl-pyrimidine, 2-cyanoamino-4,6-dimethoxypyrimidine, 2-cyanoamino-4-ethoxy-6-methyl-pyrimidine, 2-cyanoamino-4-methyl-6-propoxy-pyrimidine, 2-cyanoamino -4-methyl-6-isopropoxy-pyrimidine, 2-cyanoamino-4-methyl-6-butoxy-pyrimidine, 2-cyanoamino-4-methyl- 2-(cyano-N-methyl-amino)-4,6-dimethyl-pyrimidine, 2-(cyano-N-methyl-amino)-4-methoxy-6-methylpyrimidine, 2-cyanoamino-4,6-dimethyl-s-triazine, 2-cyanoamino- 4-methoxy-6-methyl-s-triazine, 2-cyanoamino-4,6-dimethoxy-s-triazine, 2-cyanoamino-4-ethoxy-6-methyl-striazine, 2-cyanoamino-5-chloro-4,6-dimethyl-pyrimidine and 2-cyanoamino-4,5,6-trimethyl-pyrimidine.

The compound 2-cyanoamino-4,6-dimethyl-pyrimidine of formula (II) is known (see J. Chem. Soc. 1953, 1725–1730). The compounds of the formula (II) are essentially obtained by the following two synthesis routes: (a¹) in general by reaction of alkali metal or alkaline earth metal salts of cyanamide—such as, for example, sodium cyanamide or calcium cyanamide—with halogen compounds of the formula (VII)

in which
R² has the meaning given above and
Hal¹ represents fluorine, chlorine, bromine or iodine, in particular chlorine,
if appropriate in the presence of inert diluents, such as, for example, acetone, acetonitrile or dimethylformamide, at temperatures between 0° C. and 150° C., preferably between 10° C. and 100° C.; after the volatile component has been distilled off and the residue has been dissolved in water, the cyano compounds of the formula (II) can be precipitated by acidification, for example with hydrochloric acid, and can be isolated by filtration under suction; or (a²) in the case in which $R^2$ represents a substituted pyrimidinyl radical, by reaction of cyanoguanidine ("dicyanodiamide") with β-dicarbonyl compounds, such as, for example, acetylacetone (see J. Chem. Soc. 1953, 1725-1730), acetoacetic acid esters (see J. Prakt. Chem. 77, (1908), 542 and J. Chem. Soc. 1948, 586) or malonic acid esters (see German Patent Specification No. 158,591).

The 2-cyanoamino-4-hydroxy-6-methyl- or—4,6-dihydro-pyrimidines obtained from acetoacetic acid esters or malonic acid esters can be converted to the corresponding 2-cyanoamino-4-alkoxy-6-methyl- or -4,6-dialkoxypyrimidines in a customary manner by reaction with alkylating agents, such as, for example, dimethyl sulphate or diethyl sulphate, if appropriate in the presence of diluents, such as, for example, water, methanol, ethanol, n- and iso-propanol, acetone, dioxahe or dimethylformamide, and in the presence of acid-binding agents, such as, for example, sodium hydroxide, potassium hydroxide, sodium carbonate or potassium carbonate. If necessary, in order to avoid N-alkylation, acylation is carried out with an acylating agent, such as, for example, acetic anhydride or acetyl chloride, and deacylation is effected with aqueous acids or bases after the alkylation.

The halogen compounds of the formula (VII) are known (see J. Chem. Soc. (C) 1966, 2031; Chem. Pharm. Bull. 11 (1963), 1382-1388; and Arch. Pharm. 295 (1962), 649-657).

Amino compounds of the formula (III) which are furthermore to be used as starting materials for process variant (a) are known and can be prepared by processes which are in themselves known (see Chem. Pharm. Bull. 15 (1967), 345-349; Bull. Soc. Chem. France 1958, 664; and Synthesis 1976, 682).

In formula (III), $R^4$ preferably has the same meaning as given above within the framework of the definition of substituents for formula (I) as being preferred, and $R^3$ preferably represents hydrogen, $C_1$–$C_4$-alkoxy [which is optionally substituted by fluorine, chlorine, bromine, cyano, hydroxyl or $C_1$–$C_4$-alkoxy], $C_3$–$C_6$-cycloalkyl, $C_3$–$C_6$-alkenyl, $C_3$–$C_6$-alkinyl or benzyl [which is optionally substituted by fluorine, chlorine or methyl].

Particularly preferred starting materials of the formula (III) are those in which $R^4$ has the same meaning as given above within the framework of the definition of substituents for formula (I) as being particularly preferred, and $R^3$ represents hydrogen, optionally hydroxyl-substituted $C_1$–$C_4$-alkyl, $C_5$–$C_6$-cycloalkyl, $C_3$–$C_4$-alkenyl, $C_3$–$C_4$-alkinyl or benzyl.

As starting materials of the formula (III), the following may be mentioned as examples: ammonia, methylamine, ethylamine, n- and iso-propylamine, n-, iso-, sec.- and tert.-butylamine, cyclopentylamine, cyclohexylamine, allylamine, propargylamine, benzylamine, aniline, 2-fluoro-, 3-fluoro- and 4-fluoro-aniline, 2-chloro-, 3-chloro-and 4-chloro-aniline, 2-bromo-, 3-bromo- and 4-bromo-aniline, 2-nitro-, 3-nitro- and 4-nitro-aniline, 2-amino-, 3-amino- and 4-amino-benzonitrile, 4-aminobenzenesulphonamide, ortho-, meta- and para-phenylene diamine, ortho-, meta-and para-toluidine, 2-trifluoromethyl-, 3-trifluormethyl-and 4-trifluoromethyl-aniline, 2-methoxy-, 3-methoxy- and 4-methoxy-aniline, 4-trifluoromethylthio-aniline, 2-amino and 4-amino-benzoic acid methyl ester, dimethylamine, diethylamine, dipropylamine, diisopropylamine, dibutylamine, dicyclopentylamine, dicyclohexylamine, diallylamine, dipropargylamine, dibenzylamine, N-methylaniline, O-methyl-hydroxylamine, O-ethyl-hydroxylamine, O-propylhydroxylamine, O-isopropylhydroxylamine, O-butylhydroxylamine, O-isobutyl-hydroxylamine, O-allyl-hydroxylamine, O-propargyl-hydroxylamine, O-benzyl-hydroxylamine, N,O-dimethyl-hydroxylamine, methylhydrazine, N,N-dimethylhydrazine, N,N'-dimethylhydrazine, ethylhydrazine and n- and iso-propylhydrazine as well as the hydrochlorides of these compounds; phenylhydrazine, acethydrazide, methyl hydrazinoformate, benzenesulphonohydrazide and p-toluenesulphonohydrazide.

Formula (I) and the conditions stated above under (b) give a general definition of the guanidine derivatives to be used as starting materials in process (b). In this formula—where it relates to the guanidines to be used as starting materials for process (b)

$R^1$ preferably represents hydrogen, $R^3$ preferably represents hydrogen, $C_1$–$C_4$-alkyl [which is optionally substituted by fluorine, chlorine, bromine, cyano, hydroxyl or $C_1$–$C_4$-alkoxy], $C_3$–$C_6$-cycloalkyl, $C_3$–$C_6$-alkenyl, $C_3$–$C_6$-alkinyl or benzyl [which is optionally substituted by fluorine, chlorine or methyl], M represents hydrogen, $C_1$–$C_6$-alkyl [which is optionally substituted by fluorine, chlorine or cyano], $C_3$–$C_6$-alkenyl, $C_3$–$C_6$-alkinyl or benzyl and $R^2$ and $R^4$ preferably have the same meanings as given above within the framework of the definition of substituents for formula (I) as being preferred.

Particularly preferred starting materials for process variant (b) are the guanidine derivatives of the formula (I)

in which $R^1$ represents hydrogen, $R^3$ represents hydrogen, optionally hydroxyl-substituted alkyl, $C_5$–$C_6$-cycloalkyl, $C_3$–$C_4$-alkenyl, $C_3$–$C_4$-alkinyl or benzyl, M represents hydrogen and $R^2$ and $R^4$ have the same meanings as given above within the framework of the definition of substituents for formula (I) as being particularly preferred.

The following may be mentioned as examples of guanidine derivatives of the formula (I) which are to be employed as starting materials in preparation process (b): N'-4,6-dimethyl-pyrimidin-2-yl)-, N'-4-methoxy-6-methyl-pyrimidin-2-yl)-, N'-(4-ethoxy-6-methyl-pyrimidin-2-yl)-, N'-(4-propoxy-6-methyl-pyrimidin-2-yl)-, N'-(4-isopropoxy-6-methyl-pyrimidin-2-yl) N'-(4-1-butoxy-6-methyl-pyrimidin-2-yl)-, N'-(4-isobutoxy-6-methyl-pyrimidin-2-yl)-, N'-4,6-dimethoxy-pyrimidin-2-yl) dimethyl-s-triazin-2-yl)-, N'-4-methoxy-6-methyl-s-riazin-2-yl)-, N'-(4-ethoxy-6-methyl-s-triazin-2-y N'-4,6-dimethoxy-s-triazin-2-yl)-, N'-methyl-N'-(4-methoxy-6-methyl-pyrimidin-2-yl)-, N'-(4,5,6-trimethylpyrimidin-2-yl) and N'-(5-chloro-4,6-dimethyl-pyrimidine-yl)-guanidine, -N''-methylguanidine, -N''-ethylguanidine, -N''-propyl-guanidine, -N''-isopropyl-guanidine, -N''-butyl-guanidine, -N''-isobutyl-guanidine, -N''-sec.- butyl-guanidine, -N''-tert.-butyl-guanidine, -N''-cyclopentyl-guanidine, -N''-cyclohexyl-guanidine, -N''-allylguanidine, -N''-propargyl-guanidine, -N''-benzyl-guanidine, -N''-phenyl-guanidine, -N''-(2-fluoro-phenyl)-, -(3-fluoro-phenyl)- and -(4-fluoro-phenyl)-guanidine, -N''-(2-chloro-phenyl-, -(3-chloro-phenyl)- and -(4-chloro-phenyl)-guanidine, -N''-

(2-bromo-phenyl)-, -(3-bromo-phenyl)- and -(4-bromo-phenyl)-guanidine, -N''-(2-nitro-phenyl)-, -(3-nitrophenyl)- and -(4-nitro-phenyl)guanidine, -N''-(2-aminophenyl)-, -(3-aminophenyl)- and -(4-amino-phenyl)-guanidine, -N''-(2-cyano-phenyl)-, -(3-cyano-phenyl)- and -(4-cyano-phenyl)-guanidine, -N''-(4-amino-sulphonyl-phenyl)-guanidine, -N''-(2-hydroxyphenyl)-, -(3-hydroxy-phenyl)- and -(4-hydroxy-phenyl)guanidine, -N''-2-methyl-phenyl)-, -(3-methyl-phenyl)-and -(4-methyl-phenyl)-guaridine, -N''-(2-trifluoromethylphenyl)-, -(3-trifluoromethyl-phenyl)- and -(4-trifluoromethyl-phenyl)-guanidine, -N''-2-methoxyphenyl)- -(3-methoxy-phenyl)- and -(4-methoxyphenyl)-guanidine, -N''-(2-trifluoromethoxy-phenyl)- and -(4-trifluoromethoxyphenyl)-guanidine, -N''-(4-trifluoromethylthio-phenyl)-guanidine, -N''-(2-methoxycarbonylphenyl)- and -(4-methoxycarbonyl-phenyl)-guanidine, -N'',N''-dimethyl-guanidine, -N'',N''-diethyl-guanidine, -N'',N''-dipropylguanidine, -N'',N''-diisopropyl-guanidine, -N'',N''-di- butyl-guanidine, -N'',N''-diisobutyl-guanidine. -N'',N''-dicyclopentyl-guanidine, -N'',N''-dicyclohexyl-guanidine, -N'',N''-diallyl-guanidine, -N'',N''-dipropargyl-guanidine, -N'',N''-dibenzyl-guanidine, -N''-methyl-N''-phenyl-guanidine, -N''-methoxy-guanidine, -N''-ethoxy-guanidine, -N''-propoxy-guanidine, -N''-isopropoxy-guanidine, -N''-butoxy-guanidine, -N''-isobutoxy-guanidine, -N''-allyloxy-guanidine, -N''-propargyloxy-guanidine, -N''-benzyloxy-guanidine, -N''-methyl-N''-methoxy-guanidine, -N'''-methylamino-guanidine, -N''-dimethylamino-guanidine, -N''-methyl-N'''-methylamino-guanidine, -N''-ethylamino-guanidine, -N''-propylamino-guanidine, -N''-isopropylamino-guanidine, -N'''-morpholino-guanidine, -N''-acetamino-guanidine, -N'''-methoxycarbonylamino-guanidine, -N''-benzenesulphonylamino-guanidine and -N''-p-toluenesulphonylamino-guanidine.

The guanidine derivatives of the formula (I) which are to be used as starting materials for process (b) have largely not yet been described in the literature and can be prepared by process (a) according to the invention.

Formulae (IV) and (V) give general definitions of the halogen/sulphur compounds furthermore to be used as starting materials in process (b). In these formulae, m, n, $R^5$ and $R^6$ preferably or particularly have the same meanings as given above within the framework of the definition of substituents for formula (I) as being preferred or particularly preferred respectively, and $X^1$ and $X^2$ preferably and particularly preferably represent chlorine.

The following may be mentioned as starting materials of the formulae (IV) and (V): 2-chloro-, 2-fluoro-, 2-bromo-, 2-nitro-, 2-methyl-, 2-methoxycarbonyl-, 2-ethoxycarbonyl-, 2-methoxy-, 2-ethoxy-, 2-phenyl-, 2-trifluoromethyl-, 2-difluoromethoxy-, 2-trifluoromethoxy-, 2-phenoxy-, 2-methyl-5-chloro-, 2,5-dichloro- and 2-chloro-5-trifluoromethyl-benzenesulphonyl chloride and the corresponding sulphenyl and sulphinyl chlorides.

Halogen/sulphur compounds of the formulae (IV) and (V) are known (see Chemistry Lett. 1978, 951; EP-PA Nos. 23,422, 35,893, 42,731, 44,808, 44,809, 51,466, 64,804 and 70,041; U.S. Pat. Nos. 2,929,820, 4,282,242 and 4,372,778; and J. Org. Chem. 33 (1968), 2104).

The compounds of the formulae (IV) and (V), in which m and n respectively represent the number 2, are essentially obtained by the two following methods of synthesis:

($b^1$) by reacting the corresponding sulphonic acids $R^5$—$SO_3H$ or $R^6$—$SO_3H$ or their alkali metal or alkaline earth metal salts with halogenating agents, such as, for example, phosphorus(V) chloride (phosphorus pentachloride), phosphoryl chloride (phosphoroxychloride), thionyl chloride, phosgene or benzotrichloride, if appropriate in the presence of catalysts, such as, for example, pyridine or dimethylformamide, and, if appropriate, using inert diluents, such as, for example, methylene chloride, chloroform, acetonitrile, chlorobenzene and/or sulpholane, at temperatures between −20° C. and +150° C., preferably between 0° C. and +100° C.; after dilution with water, the sulphonyl chlorides—if they are obtained in crystalline form—can be isolated by filtration under suction or can be purified by extraction with a water-immiscible solvent, such as, for example, methylene chloride, diethyl ether or hexane, washing and drying of the extracts, evaporating down and recrystallization or distillation; or ($b^2$) in the case in which $X^1$ and $X^2$ represent chlorine and $R^5$ and $R^6$ represent an aromatic radical, in a manner which is known in itself (see J. Org. Chem. 25 (1960), 1824; DE-OS (German Published Specification) No. 2,308,262 and EP-PA No. 59,241) by reacting appropriate amino compounds $R^5$-$NH_2$ and $R^6$-$NH_2$ respectively with sodium nitrite and hydrochloric acid, if appropriate in the presence of acetic acid, at temperatures between −10° C. and +20° C., preferably between −5° C. and +10° C., and then (in situ) with sulphur dioxide or a salt of sulphurous acid, such as, for example, sodium sulphite or sodium bisulphite, in the presence of a copper compound, such as, for example, copper chloride or copper sulphate, as a catalyst, at temperatures between 0° C. and 80° C., preferably between 10° C. and 60° C.

Working up can be carried out in a customary manner: on dilution with water, the sulphonyl chlorides are obtained in general in crystalline form, and can be isolated by filtering them off under suction. However, they can also be extracted from the aqueous dispersion with a solvent which is virtually water-immiscible, such as, for example, methylene chloride or diethyl ether, and can be dried, and purified by vacuum distillation.

Formula (VI) gives a definition of the isothioureas to be used as starting materials in process (c). In this formula, $R^5$ preferably represents $C_1$-$C_4$-alkyl or benzyl, in particular methyl, and $R^1$, $R^2$ and M preferably or particularly have the same meanings as given above within the framework of the definition of substituents for formula (I) as being preferred or particularly preferred.

The following may be mentioned as examples of the starting materials of the formula (VI): N'-(4,6-dimethoxy-s-triazin-2-yl)-, N'-(4,6-dimethyl-pyrimidin-2-yl)-, N'-(4-methoxy-6-methyl-pyrimidin-2-yl)-, N'-(4-ethoxy-6-methyl-pyrimidin-2-yl)-, N'-(4-propoxy-6-methyl-pyrimidin-2-yl)-, N'-(4-isopropoxy-6-methyl-pyrimidin-2-yl)-, N'-(4-butoxy-6-methyl-pyrimidin-2-yl)-, N'-(4-isobutoxy-6-methyl-pyrimidin-2-yl)-, N'-(4,6-dimethoxy-pyrimidin-2-yl)-, N'-(4,6-dimethyl-s-triazin-2-yl)-, N'-(4-methoxy-6-methyl-s-triazin-2-yl)-, N'-(4-ethoxy-6-methyl-s-triazin-2-yl)-, N'-(4,5,6-trimethyl-pyrimidin- 2-yl)- and N'-(5-chloro-4,6-dimethyl-pyrimidin-2-yl)-, -N''-(2-fluoro-benzenesulphonyl)-, -N''-(2-chloro-benzenesulphonyl)-, -N''-(2-bromo-benzenesulphonyl)-, -N''-(2-nitro-benzenesulphonyl)-, -N''-(2-methylbenzenesulphonyl)-, -N''-(2-methoxycarbonyl-benzenesulphonyl)-, -N''-(2-ethoxycarbonyl-benzenesulphonyl)-, -N''-(2-methoxy-benzenesulphonyl)-, -N''-(2-ethoxybenzenesulphonyl)-, -N''-(2-phenyl-benzenesulphonyl)-, -N''-(2-trifluoromethyl-benzenesulphonyl)-, -N''-(2-difluoromethoxy-benzenesulphonyl)-, -N''-(2-trifluoromethoxy-benzenesulphonyl)-, -N''-(2-phenoxy-benzenesulphonyl)-, -N''-(2-methyl-5-chlorobenzenesulphonyl)-, -N''-(2,5-dichloro-benzenesulphonyl)- and -N''-(2-chloro-5-trifluoromethyl-benzenesulphonyl)-S-methyl-isothiourea.

Isothioureas of the formula (VI) are known (see EP-PA No. 5,986). These compounds are obtained in a manner which is in itself known, by reacting appropriate isodithiocarbamic acid derivatives of the formula (VIII)

in which
R$^1$ and R$^{15}$ have the meanings given above,
with amino-hetarenes of the formula (IX)

M—NH—R$^2$ (IX)

in which
M and R$^2$ have the meanings given above,
if appropriate in the presence of a base which is strong but slightly nucleophilic, such as, for example, sodium hydride, and, if appropriate, in the presence of a diluent, such as, for example, tetrahydrofuran, dioxane, 1,2-dimethoxyethane, dimethylformamide or dimethyl sulphoxide, at temperatures between −20° C. and 100° C., preferably between 0° C. and +80° C. Working up can be carried out by customary methods, for example by dilution with water and acidification, for example with hydrochloric acid, after which the products of the formula (VI), which are obtained in crystalline form, can be isolated by filtration under suction.

Formula (VIII) gives a definition of the isodithiocarboxylic acid derivatives required as intermediate products. In this formula, R$^1$ and R$^{15}$ preferably or particularly have the same meanings as given above within the framework of the definition of substituents for formula (I) or (VI) as being preferred or particularly preferred.

The following may be mentioned as examples of the compounds of the formula (VIII): N-(2-fluoro-benzenesulphonyl), N-(2-chloro-benzenesulphonyl), N-(2-bromobenzenesulphonyl), N-(2-nitro-benzenesulphonyl), N-(2-methyl-benzenesulphonyl), N-(2-methoxycarbonyl-benzenesulphonyl), N-(2-ethoxycarbonyl-benzenesulphonyl), N-(2-methoxy-benzenesulphonyl), N-(2-ethoxy-benzenesulphonyl), N-(2-phenyl-benzenesulphonyl), N-(2-difluoromethoxybenzenesulphonyl), N-(2-trifluoromethoxy-benzenesulphonyl), N-(2-phenoxy-benzenesulphonyl), N-(2-methyl-5-chlorobenzenesulphonyl), N-(2,5-dichloro-benzenesulphonyl) and N-(2-chloro-5-trifluoromethyl-benzenesulphonyl) S',S''-dimethyl isodithiocarbamate.

The isodithiocarbamic acid derivatives of the formula (VIII) largely have not yet been described in the literature. These compounds are obtained in a manner which is in itself known (see Chem. Ber. 99 (1966), 2885) by reacting amino compounds of the formula (X)

R$^1$—NH$_2$ (X)

in which

R$^1$ has the meaning given above,
with carbon disulphide in the presence of a strong base, such as, for example, sodium hydroxide, and, if appropriate, in the presence of diluents, such as, for example, water and dimethylformamide, at temperatures between −20° C. and +150° C., preferably between 0° C. and 100° C., followed by reaction (in situ) with an alkylating agent of the formula (XI)

Hal$^2$—R$^{15}$ (XI)

in which
R$^{15}$ has the meaning given above and
Hal$^2$ represents chlorine, bromine or iodine,
at temperatures between −20° C. and +150° C., preferably between 0° C. and 100° C.

The products of the formula (VIII), which are obtained in crystalline form after dilution with water, can be isolated by filtration under suction.

In formula (X), R$^1$ preferably or particularly has the same meaning as given above within the framework of the definition of substituents for formula (I) as being preferred or particularly preferred.

The following may be mentioned is examples of the compounds of the formula (X): 2-fluoro-, 2-chloro-, 2-bromo-, 2-nitro-, 2-methyl-, 2-methoxycarbonyl-, 2-ethoxycarbonyl-, 2-methoxy-, 2-ethoxy-, 2-phenyl-, 2-difluoromethoxy-, 2-trifluoromethoxy-, 2-phenoxy-, 2-methyl-5-chloro-, 2,5-dichloro- and 2-chloro-5-trifluoromethylbenzenesulphonamide.

Some of the amino compounds of the formula (X) are known (see EP-PA Nos. 23,422, 30,140, 35,893, 44,807, 44,808, 44,809, 51,466, 64,804, 70,041 and 70,802; and U.S. Pat. No. 4,372,778).

These compounds are obtained in a manner which is in itself known, by reacting appropriate chlorine compounds R$^1$-Cl with ammonia, if appropriate using inert diluents, such as, for example, diethyl ether or tetrahydrofuran, at temperatures between −20° C. and +100° C., preferably between 0° C. and 50° C. The products of the formula (X), which are obtained in crystalline form in this procedure, can be isolated by filtration under suction.

Examples of suitable precursors of the formula R$^1$-Cl and methods of preparing these are given above in the description of the starting materials for process (b).

In formula (XI), R$^1$ preferably represents $C_1$-$C_4$-allyl or benzyl, in particular methyl, and Hal$^2$ represents chlorine, bromine or iodine.

The following may be mentioned as examples of compounds of the formula (XI): methyl chloride, methyl bromide, methyl iodide, ethyl chloride, ethyl bromide and ethyl iodide, as well as benzyl chloride and benzyl bromide.

The compounds of the formula (XI) are known.

Formula (IX) gives a definition of the aminohetarenes furthermore to be used as intermediate products. In this formula, R$^2$ preferably or particularly represents the same radicals as given within the framework of the definition of substituents for formula (I) as being preferred or particularly preferred, and M preferably represents hydrogen, sodium or potassium or one equivalent of magnesium or calcium, in particular hydrogen.

The following may be mentioned as examples of the compounds of the formula (IX): 4,6-dimethyl-, 4,5,6-trimethyl-, 5-chloro-4,6-dimethyl-, 4-methoxy-6-methyl-, 4-ethoxy-6-methyl-, 4-propoxy-6-methyl-, 4-isopropoxy-6-methyl-, 4-butoxy-6-methyl-, 4-isobutoxy-6- methyl- and 4,6-dimethoxy-2-amino-pyrimidine as well as 4,6-dimethyl-, 4-methoxy-6-methyl-, 4-ethoxy-6-methyl- and 4,6-dimethoxy-2-amino-s-triazine.

Compounds of the formula (IX) are known and can be prepared by processes which are in themselves known (see Chem. Pharm. Bull. 11 (1963), 1382–1388; and U.S. Pat. No. 4,299,960).

Formula (III) gives a definition of the amino compounds furthermore to be used as starting materials in process (c) according to the invention. The preferred and particularly preferred meanings of the formula (III) are listed above within the framework of the description of the starting materials for process (a).

Formula (I) and the conditions stated above under (d) give general definitions of the guanidine derivatives to be used as starting materials in process (d).

In formula (I)—where it relates to the guanidine derivatives to be used as starting materials for process (d)—$R^1$ and $R^3$ preferably represent the radicals —S-(O)$_m$—$R^5$ and —S(O)$_n$—$R^6$ respectively, wherein m and n and $R^5$ and $R^6$ preferably or particularly have the same meanings as given above within the framework of the definition of substituents for formula (I) as being preferred or particularly preferred; furthermore, $R^2$, $R^4$ and M preferably or particularly have the same meanings as given above within the framework of the definition of substituents for formula (I) as being preferred or particularly preferred.

The following may be mentioned as examples of the compounds of the formula (I) which are to be used as starting materials in process (d): N'-(4,6-dimethylpyrimidin-2-yl)-N"-methoxy-N"',N"''-bis-(2-chlorobenzenesulphonyl)-, -N",N"''-bis-(2-bromo-benzenesulphonyl)-, -N",N"''-bis-(2-fluoro-benzenesulphonyl)-, -N",N"''-bis-(2-methoxy-benzenesulphonyl)-, -N",N"''-bis-(2-methyl-benzenesulphonyl)- and -N",N"''-bis-(2-methoxycarbonyl-benzenesulphonyl)-guanidine.

The guanidine derivatives of the formula (I) which are to be used as starting materials for process (d) have not been described in the literature hitherto. They can be obtained by the preparation processes described above under (b).

Formula (III) gives a definition of the amino compounds furthermore to be used as starting materials in process (c) according to the invention. The preferred and particularly preferred meanings of $R^3$ and $R^4$, as well as examples of compounds of the formula (III), are iven above in the description of the starting materials for process (a).

Formula (I) and the conditions stated above under (c) give definitions of the guanidine derivatives to be used as starting materials in process (e). In formula (I)—where it relates to guanidine derivatives to be used as starting materials for process (e)—M represents hydrogen and the radicals $R^1$, $R^2$, $R^3$ and $R^4$ preferably or particularly have the same meanings as given above within the framework of the definition of substituents for formula (I) as being preferred or particularly preferred.

The following may be mentioned as examples of compounds of the formula (I) which are to be used as starting materials in process (e): N'-(4,6-dimethylpyrimidin-2-yl)-N"-methoxy-N"',N"''-bis-(2-fluorobenzenesulphonyl)-, -N",N"''-bis-(2-chloro-benzenesulphonyl)-, -N",N"''-bis-(2-bromo-benzenesulphonyl)-, -N",N"''-bis-(2-methoxy-benzenesulphonyl)-, -N",N"''-bis-(2-methyl-benzenesulphonyl)- and -N",N"''-bis-(2-methoxycarbonyl-benzenesulphonyl)-guanidine as well as N'-(4,6-dimethyl-pyrimidin-2-yl)-N"-methoxy-N"''-(2-fluoro-benzenesulphonyl)-, -N"'',-(2-chloro-benzenesulphonyl)-, -N"''-(2-bromo-benzenesulphonyl)-, -N"''-(2-methyl-benzenesulphonyl)-, -N"''-(2-methoxy-benzenesulphonyl)- and -N"''-(2-methoxycarbonyl-benzenesulphonyl)-guanidine.

The guanidine derivatives of the formula (I) which are to be used as starting materials for process (e) have not been described in the literature hitherto. They can be obtained by the preparation processes described above under (a), (b), (c) and (d).

The following may be mentioned as examples of metal hydroxides, hydrides or alkanolates or organometallic compounds which are to be used for process (e): lithium hydroxide, sodium hydroxide, potassium hydroxide, magnesium hydroxide and calcium hydroxide, lithium hydride, sodium hydride and calcium hydride, sodium methylate and ethylate, potassium methylate and ethylate and potassium tert.-butylate, as well as butyl-lithium and isopropyl-magnesium chloride.

The following may be mentioned as examples of the amines which may, if appropriate, be used in process (e): isopropylamine, diisopropylamine, isobutylamine, sec.-butylamine, tert.-butylamine, diisobutylamine, trimethylamine, triethylamine, dibenzylamine and ethyldiisopropylamine.

Formula (I) gives a definition of the guanidine derivatives to be used as starting materials in process (f). In formula (I), $R^1$, $R^2$, $R^3$, $R^4$ and M preferably or particularly have the same meanings as given above within the framework of the definition of substituents for formula (I) as being preferred or particularly preferred. Examples of compounds of the formula (I), which can also be used as starting materials in process (f), are given above in the description of the starting materials for process (e).

In process (f), strong acids are employed as starting materials. These are preferably hydrohalic acids, such as hydrogen fluoride, hydrogen chloride, hydrogen bromide and hydrogen iodide, and furthermore sulphuric acid and phosphoric acid or alkanesulphonic acids which have up to 4 carbon atoms and are optionally substituted by fluorine or chlorine, such as, for example, methanesulphonic acid, ethanesulphonic acid, chloromethanesulphonic acid, 2-chloroethanesulphonic acid and trifluoromethanesulphonic acid, and also benzenesulphonic acid, p-toluenesulphonic acid, naphthalene-1-sulphonic acid, naphthalene-2-sulphonic acid, naphthalene-1,4-. -1,5-, -1,6-, -2,6- and -2,7-disulphonic acid. Hydrochloric acid (hydrogen chloride), sulphuric acid, benzenesulphonic acid and p-toluenesulphonic acid are particularly preferred.

Process (a) is preferably carried out using diluents. Suitable diluents are all inert organic solvents. Alcohols, such as, for example, methanol, ethanol, n- and iso-propanol, and n-, iso-, sec.- and tert.-butanol, are particularly suitable. Ethanol is particularly preferred as the solvent.

Virtually all customarily used acid-binding agents can be employed as acid acceptors. These include, in particular, alkali metal and alkaline earth metal hydroxides, alkali metal and alkaline earth metal carbonates, ammonia (if appropriate aqueous ammonia), and aliphatic, aromatic or heterocyclic amines, such as triethylamine, N,N-dimethylaniline, N,N-dimethyl-benzylamine, pyridine, diazabicyclooctane and diazabicycloundecene (DBU).

In process (a), the reaction temperature can be varied within a relatively wide range. In general, the reaction is carried out at between 0° C. and 150° C., preferably between 20° C. and 120° C. Process (a) is generally carried out under atmospheric pressure.

To carry out process (a) according to the invention, in general between 0.5 and 5 mols, preferably between 1 and 3 mols, of amino compound of the formula (III) or of its hydrochloride are employed per mol of cyano compound of the formula (II).

The starting materials of the formulae (II) and (III) and, if appropriate, the diluent are generally combined at room temperature or with slight external cooling, and the reaction mixture is stirred, if appropriate at elevated temperature, until the reaction is complete.

Working up and isolation of the new compounds of the formula (I) are carried out by customary methods: the solution is diluted—if appropriate after cooling and if appropriate after filtration—with water, or is evaporated down in vacuo and the residue dissolved in water, and the solution, if necessary after filtration, is brought, if required, to a slightly alkaline pH value by addin one of the abovementioned acid acceptors. The products of the formula (I) are obtained in crystalline form in this procedure, and can be isolated by filtration under suction.

Process (b) according to the invention, for the preparation of the new compounds of the formula (I), is preferably carried out using diluents.

Suitable diluents are virtually all inert organic solvents, but aprotic polar solvents are preferred. These include optionally halogenated hydrocarbons, such as, for example, methylene chloride, chloroform, toluene and chlorobenzene, nitriles, such as, for example, acetonitrile and propionitrile, dimethylformamide, dimethylacetamide, dimethyl sulphoxide, sulpholane, hexamethylphosphoric acid triamide, 1,2-dimethoxyethane, pyridine and 2-methyl-5-ethyl-pyridine.

Virtually all customarily used acid-binding agents can be employed as acid acceptors in process (b). These include, in particular, alkali metal and alkaline earth metal hydroxides, alkali metal and alkaline earth metal hydrides, organometallic compounds, such as butyllithium, and also aliphatic, aromatic or heterocyclic amines, such as trimethylamine, triethylamine, N,N-dimethylaniline, N,N-dimethyl-benzylamine, diazabicyclooctane (DABCO), diazabicycloundecene (DBU), pyridine and 2-methyl-5-ethyl-pyridine.

In process (b), the reaction temperatures can be varied within a relatively wide range. In general, the reaction is carried out at between −80° C. and +100° C., preferably between −30° C. and +50° C. Process (b) according to the invention is carried out in general under atmospheric pressure.

To carry out process (b) according to the invention, in general between 0.5 and 5 mols, preferably between 1 and 3 mols, of halogen/sulphur compound of the formula (IV) or (V) are employed per mol of guanidine intermediate product of the formula (I).

The reaction components are usually combined at room temperature or with external cooling, and the reaction mixture is stirred until the reaction is complete.

Working up and isolation of the new compounds are carried out by customary methods: the mixture is shaken with water and a water-immiscible solvent, such as, for example, methylene chloride, chloroform or toluene, if appropriate after volatile components have been distilled off, and the organic phase is washed with water, dried, filtered and evaporated down. The products of the formula (I) which remain in the residue are crystallised by digestion with organic solvents, such as, for example, diethyl ether, ethyl acetate, ethanol or isopropanol, and if required are purified by recrystallization.

Process (c) according to the invention, for the preparation of compounds of the formula (I), is preferably carried out using diluents. Suitable diluents are virtually all inert organic solvents. These include, in particular, optionally chlorinated hydrocarbons, such as, for example, chloroform, carbon tetrachloride, toluene, xylene, chlorobenzene and 1,2-dichlorobenzene, ethers, such as, for example, diisopropyl ether and dibutyl ether, tetrahydrofuran, dioxane, 1,2-dimethoxyethane and diglycol dimethyl ether (diglyme), nitriles, such as, for example, acetonitrile and propionitrile, as well as dimethylformamide, dimethylacetamide, dimethyl sulphoxide and sulpholane.

Acid-binding agents which have nucleophilic properties which do not compete significantly with those of the amino compounds of the formula (III) are employed as acid acceptors in process (c). Examples of acid acceptors which may be mentioned are alkali metal and alkaline earth metal carbonates, such as, for example, potassium carbonate and calcium carbonate, tertiary amines, such as, for example, triethylamine, N,N-dimethylaniline and N,N-dimethylbenzylamine, as well as nitrogen heterocycles, such as, for example, pyridine, diazabicyclooctane (DABCO) and diazabicycloundecene (DBU).

In process (c), the reaction temperature can be varied within a relatively wide range. In general, the reaction is carried out at between 0° C. and 200° C., preferably between 20° C. and 120° C. Process (c) is carried out in general under atmospheric pressure.

To carry out process (c) according to the invention, in general between 1 and 5 mols preferably between 1 and 3 mols of amino compound of the formula (III) or its hydrochloride are employed per mol of isothiourea of the formula (VI).

In general, the isothioureas of the formula (VI) and the diluent are initially introduced at room temperature, and the amino compounds of the formula (III), or their hydrochlorides, and suitable acid acceptors are metered in. The reaction mixture is then stirred, in general at an elevated temperature, until the reaction is complete. On cooling, the products of the formula (I) are usually obtained in crystalline form, and can be isolated by filtration under suction. If the products of the formula (I) are obtained in the form of ammonium salts, the corresponding acids (M=H) can be prepared from these ammonium salts by dissolving them in water and acidifying the solution, for example with hydrochloric acid or sulphuric acid.

Process (d) according to the invention is preferably carried out using diluents. Suitable diluents are virtually all inert organic solvents and, where appropriate, also water. These include, in particular, alcohols, such as methanol, ethanol and n- and iso-propanol, ethers, such as tetrahydrofuran, dioxane and 1,2-dimethoxyethane, esters, such as methyl acetate and ethyl acetate, nitriles, such as, for example, acetonitrile and propionitrile, and dimethylformamide and water.

Acid-binding agents which have nucleophilic properties which do not compete significantly with those of the amino compounds of the formula (III) can be employed as acid acceptors in process (d).

Acid acceptors which may be mentioned are alkali metal and alkaline earth metal carbonates, such as, for example, potassium carbonate and calcium carbonate, tertiary amines, such as, for example, triethylamine, N,N,dimethylaniline and N,N-dimethylbenzylamine, and nitrogen heterocycles, such as, for example, pyridine, diazabicyclooctane (DABCO) and diazabicycloundecene (DBU).

In process (d), the reaction temperature can be varied within a relatively wide range. In general, the reaction is carried out at between 0° C. and 150° C., preferably between 10° C. and 100° C.. Process (d) is carried out in general under atmospheric pressure.

To carry out process (d) according to the invention, in general between 1 and 10 mols, preferably between 2 and 5 mols, of amino compound of the formula (III) or its hydrochloride are employed per mol of guanidine intermediate product of the formula (I).

In general, the guanidine derivatives of the formula (I) and the diluent are initially introduced at room temperature or with slight cooling, and the amino compound of the formula (III), or its hydrochloride, and suitable acid acceptors are metered in. The reaction mixture is then stirred, in general at room temperature or an elevated temperature, until the reaction is complete.

Working up can be carried out by customary methods. If the products of the formula (I) are obtained from the reaction mixture in crystalline form, they can be isolated by filtration under suction. Otherwise, the mixture, if necessary after being evaporated down, is diluted with water and extracted with a solvent which is virtually water-immiscible, such as, for example, methylene chloride. By washing the extraction solution with water, drying, filtering, evaporating down the filtrate and recrystallising the residue, the products of the formula (I) can be obtained in pure form.

Process (e) according to the invention is preferably carried out using diluents. Suitable diluents are virtually all inert organic solvents. These include, in particular, alcohols, such as, for example, ethanol and n- and iso-propanol, ethers, such as, for example, tetrahydrofuran, dioxane and 1,2-dimethoxyethane, esters, such as, for example, methyl acetate and ethyl acetate, and nitriles, such as, for example, acetonitrile.

In process (e), the reaction temperature can be varied within a relatively wide range. In general, the reaction is carried out at between −20° C. and +50° C., preferably between 0° C. and 30° C. Process (e) is carried out in eneral under atmospheric pressure.

To carry out process (e) according to the invention, in general between 0.9 and 1.2 mols, preferably between 0.95 and 1.1 mols of metal compound or amine are employed per mol of guanidine derivative of the formula (I).

In general, the guanidine derivatives of the formula (I) and the diluent are initially introduced and—if appropriate with slight external cooling—the metal compound or the amine—if appropriate dissolved in the diluent—is metered in. The reaction mixture is stirred until the reaction is complete. The salt-like products of the formula (I) are obtained in general in crystalline form, and can be isolated by filtration under suction.

Process (f) according to the invention is preferably carried out using diluents. Suitable diluents are virtually all organic solvents. These include, in particular, alcohols, such as methanol, ethanol and n- and iso-propanol, ethers, such as tetrahydrofuran, dioxane and 1,2-dimethoxyethane, and esters, such as methyl acetate and ethyl acetate.

If the acids used as starting materials are employed in aqueous solution, acetic anhydride can also advantageously be used as a diluent.

In process (f), the reaction temperature can be varied within a relatively wide range. In general, the reaction is carried out at between −20° C. and +50° C., preferably between 0° C. and 30° C. Process (f) is carried out in general under atmospheric pressure.

To carry out process (f) according to the invention, in general between 1 and 10 mols preferably between 1.5 and 5 mols, of a strong acid are employed per mol of guanidine derivative of the formula (I).

In general, the guanidine derivatives of the formula (I) and the diluent are initially introduced and —if appropriate with slight external cooling—the strong acid is metered in. The reaction mixture is stirred until the reaction is complete. The 1:1 adducts are obtained in general in crystalline form, and can be isolated by filtration under suction.

The active compounds according to the invention influence plant growth and can therefore be used as defoliants, desiccants, agents for destroying broad-leaved plants and germination inhibitors, and especially as weedkillers, and also as plant rowth regulators. By weeds, in the broadest sense, there are to be understood all plants which row in locations where they are undesired. Whether the substances according to the invention act as total or selective herbicides or as plant growth regulators depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention also engage in the metabolism of the plants and, as already mentioned, can therefore be employed as growth regulators, with certain preconditions.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

Plant growth regulating compounds can be employed, for example, to inhibit vegetative growth of the plants. Such inhibition of growth is inter alia of economic interest in the case of grasses, since it is thereby possible to reduce the frequency of cutting the grass in ornamental gardens, parks and sportsgrounds, at verges, at airports or in fruit orchards. The inhibition of growth of herbaceous and woody plants at verges and in the vicinity of pipelines or overland lines or, quite generally, in areas in which heavy additional growth of plants is undesired, is also of importance.

The use of growth regulators to inhibit the growth in length of cereals is also important. The danger of lodging of the plants before harvesting is thereby reduced or completely eliminated. Furthermore, growth regulators can strengthen the stem of cereals, which again counteracts lodging. Use of growth regulators for shortening and strengthening the stem enables higher amounts of fertiliser to be applied to increase the yield, without danger of the cereal lodging.

In the case of many crop plants, inhibition of the vegetative growth makes denser planting possible, so that greater yields per area of ground can be achieved. An advantage of the smaller plants thus produced is also that the crop can be worked and harvested more easily.

Inhibition of the vegetative growth of plants can also lead to increases in yield, since the nutrients and assimilates benefit blossoming and fruit formation to a reater extent than they benefit the vegetative parts of plants.

Promotion of vegetative growth can also frequently be achieved with growth regulators. This is of great utility if it is the vegetative parts of the plants which are harvested. Promoting the vegetative growth can, however, also simultaneously lead to a promotion of generative growth, since more assimilates are formed, so that more fruit, or larger fruit, is obtained.

Increases in yield can in some cases be achieved by affecting the plant metabolism, without noticeable changes in vegetative growth. A change in the composition of plants, which in turn can lead to a better quality of the harvested products, can furthermore be achieved with growth regulators. Thus it is possible, for example, to increase the content of sugar in sugar beet, sugar cane, pineapples and citrus fruit or to increase the protein content in soya beans or cereals. Using growth regulators it is also possible, for example, to inhibit the degradation of desired constituents, such as, for example, sugar in sugar beet or sugar cane, before or after harvesting. It is also possible favourably to influence the production or the efflux of secondary plant constituents. The stimulation of latex flux in rubber trees may be mentioned as an example.

Parthenocarpous fruit can be formed under the influence of growth regulators. Furthermore, the gender of the flowers can be influenced. Sterility of the pollen can also be produced, which is of great importance in the breeding and preparation of hybrid seed.

Branching of plants can be controlled by using growth regulators. On the one hand, by breaking the apical dominance the development of side shoots can be promoted, which can be very desirable, especially in the cultivation of ornamental plants, also in connection with growth inhibition. On the other hand, however, it is also possible to inhibit the growth of side shoots. There is great interest in this action, for example, in the cultivation of tobacco or in the planting of tomatoes.

The amount of leaf on plants can be controlled under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The shedding of fruit can also be controlled with growth regulators. On the one hand, it is possible to prevent premature shedding of fruit. However, on the other hand, shedding of fruit, or even the fall of blossom, can be promoted up to a certain degree (thinning out) in order to interrupt the alternance. By alternance there is understood the peculiarity of some varieties of fruit to produce very different yields from year to year, for endogenic reasons. Finally, using growth regulators it is possible to reduce the force required to detach the fruit at harvest time so as to permit mechanical harvesting or facilitate manual harvesting.

Using growth regulators, it is furthermore possible to achieve an acceleration or retardation of ripening of the harvest product, before or after harvesting. This is of particular advantage, since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators, it is furthermore possible to influence the latent period of seeds or buds of plants, so that the plants, such as, for example, pineapple or ornamental plants in nurseries, germinate, shoot or blossom at a time at which they normally show no readiness to do so. Retarding the shooting of buds or the germination of seeds with the aid of growth regulators can be desirable in regions where frost is a hazard, in order to avoid damage by late frosts.

Finally, the resistance of plants to frost, drought or a high salt content in the soil can be induced with growth regulators. Cultivation of plants in regions which are usually unsuitable for this purpose thereby becomes possible.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example, ground natural minerals, such as kaolins, clays, talc, chalk, quartz, attapulgite, montmorillonite or diatomaceous earth, and ground synthetic minerals, such as highly dispersed silicic acid, alumina and silicates. As solid carriers for granules there are suitable: for example, crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example, non-ionic and anionic emulsifiers, such as polyoxyethylene-fatty acid esters, polyoxyethylene-fatty alcohol ethers, for example alkylaryl polyglycol ethers; alkylsulphonates, alkylsulphates, arylsulphonates as well as albumin hydrolysis products. As dispersing agents there are suitable: for example, ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use dyestuffs such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, and also as mixtures with fertilizers and other growth regulators.

Suitable herbicides for the mixtures are known herbicides, such as, for example, 1-amino-6-ethylthio-3-(2,2-dimethylpropyl)-1,3,5-triazine-2,4(1H,3H)-dione or N-(2-benzothiazolyl)-N,N'-dimethyl-urea for combating weeds in cereals; 4-amino-3-methyl-6-phenyl-1,2,4-triazin-5(4H)-one for combating weeds in sugar beet and 4-amino-6-(1,1-dimethylethyl)-3-methylthio-1,2,4-triazin-5(4H)-one for combating weeds in soybeans. Surprisingly, some mixtures also have a synergistic effect.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomizing, scattering, dusting, foaming, coating and the like. Furthermore, it is possible to apply the active compounds in accordance with the ultra-low volume process or to inject the active compound preparation or the active compound itself into the soil. It is also possible to treat the seeds of plants.

The active compounds according to the invention can be applied before as well as after emergence of the plants. They are preferably applied before emergence of the plants, that is to say by the pre-emergence method. They can also be incorporated into the soil before sowing.

The amount of active compound applied can vary within a substantial range. It depends essentially on the type of effect desired. In general, the amounts applied are between 0.001 and 10 kg of active compound per ha, preferably between 0.01 and 5 kg/ha.

As regards the time of application, the rule is that the growth regulators are applied within a preferred period of time, the exact definition of which depends on the climatic and vegetative circumstances.

The examples which follow serve to illustrate the invention further.

Preparation Examples

EXAMPLE 1

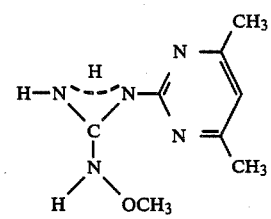

(Process a)

A mixture of 109 g (0.67 mol) of O-methylhydroxylamine hydrochloride, 99 g (0.67 mol) of 2-cyanoamino-4,6-dimethylpyrimidine and 600 ml of ethanol is heated at the boil under reflux for 7 hours. Thereafter, the alcohol is distilled off in the vacuum from a water jet, the residue is dissolved in hot water, and 100 ml of concentrated ammonia are added to this solution. The product which crystallizes out is filtered off under suction and recrystallized from ethanol.

71.8 g (55% of theory) of N'-(4,6-dimethylpyrimidin-2-yl)-N''-methoxy-guanidine of melting point 134° C. to 136° C. are obtained.

EXAMPLE 2

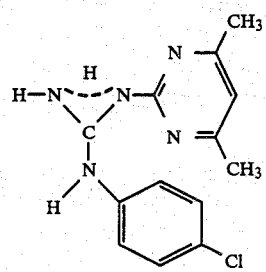

(Process a)

A mixture of 7.7 g (0.06 mol) of 4-chloroaniline hydrochloride, 7.4 g (0.05 mol) of 2-cyanoamino-4,6-dimethyl-pyrimidine and 150 ml of ethanol is heated at the boil under reflux for 15 hours. After cooling, the reaction mixture is diluted with 150 ml of water, and is rendered alkaline with 2N sodium hydroxide solution. The product which crystallizes out is filtered off under suction.

8.3 g (60% of theory) of N'-(4,6-dimethylpyrimidin-2-yl)-N''-(4-chlorophenyl)-guanidine of melting point 203° C. are obtained.

EXAMPLE 3

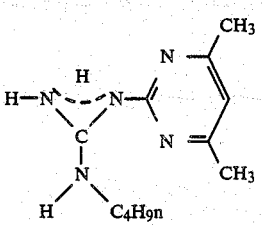

(Process a)

45 g (0.65 mol) of n-butylamine are added dropwise to a solution of 45 g (0.3 mol) of 2-cyanoamino-4,6-dimethyl-pyrimidine in 300 ml of ethanol, and the mixture is heated at the boil under reflux for 15 hours. After cooling, the mixture is filtered, and about 1.5 liters of water are added to the filtrate. The product which crystallizes out is filtered off under suction.

59.5 g (96% of theory) of N'-(4,6-dimethylpyrimidin-2-yl)-N''-butyl-guanidine of melting point 185° C. are obtained.

EXAMPLE 4

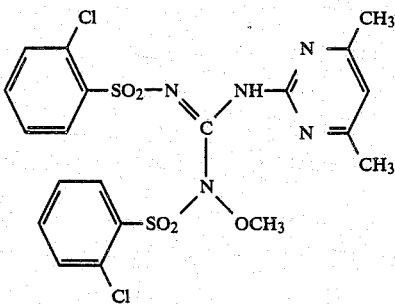

(Process b)

A mixture of 29.4 g (0.15 mol) of N'-(4,6-dimethyl-pyrimidin-2-yl)-N''-methoxy-guanidine, 63.6 g (0.3 mol) of 2-chloro-benzenesulphonyl chloride and 150 ml of pyridine is stirred for 2 days at 20° C. After the pyridine has been substantially distilled off in the vacuum from a water jet, 200 ml of water are added to the residue and the mixture is extracted with 200 ml of methylene chloride. The organic phase is separated off, dried and evaporated down. The residue is brought to crystallization by digestion with ethanol.

41.2 g (51% of theory) of N'-(4,6-dimethylpyrimidin-2-yl)-N'''-methoxy-N'',N'''-bis-(2-chlorobenzenesulphonyl)-guanidine of melting point 164° C. to 166° C. are obtained.

The above structural formula applies to the crystalline state, and is confirmed by X-ray structure analysis. Other spectroscopic data (IR, $^1$H- and $^{13}$C-NMR) and elemental analysis support the assignment of this structure.

EXAMPLE 5

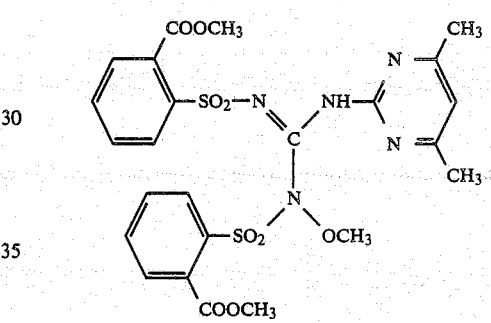

(Process b)

113 g (0.48 mol) of 2-methoxycarbonyl-benzenesulphonyl chloride are added to a mixture, cooled to −10° of 35.1 g (0.18 mol) of N'-(4,6-dimethylpyrimidin-2-yl)-N''-methoxy-guanidine and 160 ml of pyridine, and the reaction mixture is stirred for two days at 20° C. After the pyridine has been substantially distilled off in the vacuum from a water jet, 200 ml of water are added to the residue and the mixture is extracted with 200 ml of methylene chloride. The organic phase is separated off, dried with sodium sulphate, filtered and evaporated down. The residue is brought to crystallization by digestion with isopropanol.

59 g (55% of theory) of N'-(4,6-dimethyl-pyrimidin-2-yl)-N''-methoxy-N'',N'''-bis-(2-methoxycarbonylbenzenesulphonyl)-guanidine of melting point 165° C. are obtained.

The above structural formula applies to the crystalline state, and is confirmed by X-ray structure analysis. Other spectroscopic data (IR, $^1$H- and $^{13}$C-NMR) and elemental analysis support the assignment of this structure.

EXAMPLE 6

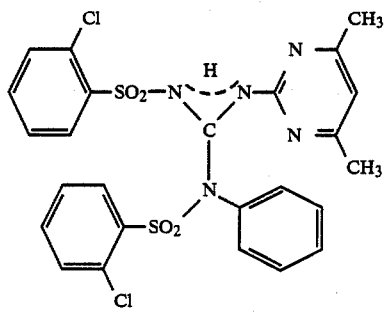

(Process b)

21.2 g (0.1 mol) of 2-chloro-benzenesulphonyl chloride are added dropwise to a mixture of 12.1 g (0.05 mol) of N'-(4,6-dimethyl-pyrimidin-2-yl)-N''-phenyl-guanidine, 10.5 g (0.1 mol) of triethylamine and 100 ml of chloroform at 20° C., and the reaction mixture is stirred for 15 hours at 20° C. Thereafter, the reaction mixture is shaken with water, and the organic phase is separated off and evaporated down. The residue is suspended in ethanol, the suspension is filtered, the filtrate is evaporated down and the residue is brought to crystallization by digestion with ethyl acetate.

6.6 g (22% of theory) of N'-(4,6-dimethylpyrimidin-2-yl)-N''-phenyl-N'',N'''-bis-(2-chloro-benzenesulphonyl)-guanidine of melting point 120° C. are obtained.

EXAMPLE 7a

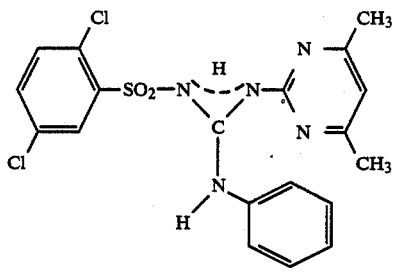

EXAMPLE 7b

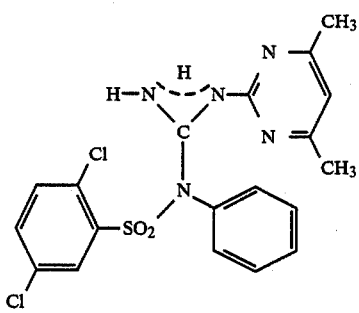

(Process b)

12.2 g (0.05 mol) of 2,5-dichloro-benzenesulphonyl chloride are added to a mixture of 12.1 g (0.05 mol) of of N'-(4,6-dimethyl-pyrimidin-2-yl)-N'''-phenyl-guanidine, 5.1 g (0.05 mol) of triethylamine and 150 ml of chloroform at 0° C. to 10° C., and the reaction mixture is stirred for 15 hours at 20° C. Thereafter, the reaction mixture is washed with 100 ml of 5% strength hydrochloric acid and is evaporated down, the residue is digested with ethanol, and the product is filtered off under suction.

3.5 g (16% of theory) of N'-(4,6-dimethylpyrimidin-2-yl)-N''-phenyl-N'''-(2,5-dichloro-benzenesulphonyl)-guanidine (7a) of melting point 188° C. are obtained.

The product which gradually crystallizes out from the mother liquor is isolated after a few days by filtering it off under suction. 1.8 g (8% of theory) of N'-(4,6-dimethyl-pyrimidin-2-yl)-N''-phenyl-N'''-(2,5-dichloro-benzenesulphonyl)-guanidine (7b) of melting point 153° C. are obtained.

EXAMPLE 8

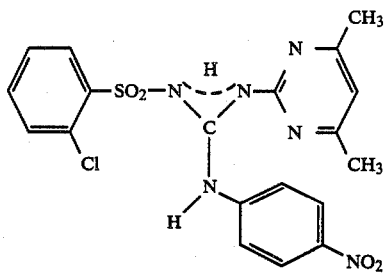

(Process b)

1.6 g (0.055 mol) of 80% strength sodium hydride are added in portions to a solution of 14.3 g (0.05 mol) of N'-(4,6-dimethyl-pyrimidin-2-yl)-N''-(4-nitrophenyl)-guanidine in 150 ml of dimethylformamide at 20° C. to 30° C., and the mixture is stirred for 15 hours at 20° C. Thereafter, 10.6 g (0.05 mol) of 2-chloro-benzenesulphonyl chloride are added dropwise, and the reaction mixture is stirred for 15 hours at 20° C. Thereafter, 500 ml of 5% strength hydrochloric acid are added. The product, which is obtained in crystalline form, is filtered off under suction.

9.4 g (41% of theory) of N'-(4,6-dimethylpyrimidin-2-yl)-N''-(4-nitrophenyl)-N'''-(2-chlorobenzenesulphonyl)-guanidine of melting point 220° C. are obtained.

EXAMPLE 9

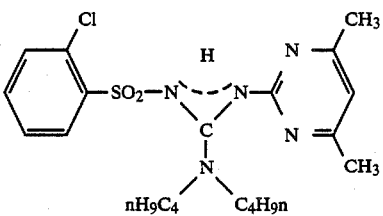

(Process b)

5.3 g (0.025 mol) of 2-chloro-benzenesulphonyl chloride are added dropwise to a mixture of 7.3 g (0.025 mol) of N'-(4,6-dimethyl-pyrimidin-2-yl)-N'',N'''-dibutylguanidine and 5.3 g (0.05 mol) of triethylamine at 20° C. The reaction mixture is ttirred for 15 hours at 20° C., and is then washed with 100 ml of 5% strength hydrochloric acid and evaporated down. The residue is brought to crystallization by digestion with ethanol.

1.8 g (16% of theory) of N'-(4,6-dimethyl-pyrimidin-2-yl)-N'',N'''-dibutyl-N'''-(2-chloro-benzenesulphonyl)-guanidine of melting point 150° C. are obtained.

EXAMPLE 10a

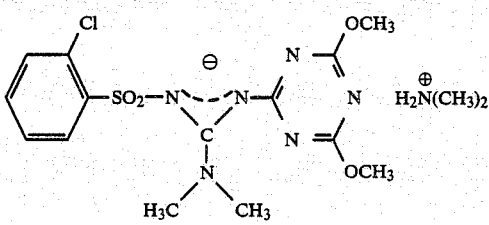

EXAMPLE 10b

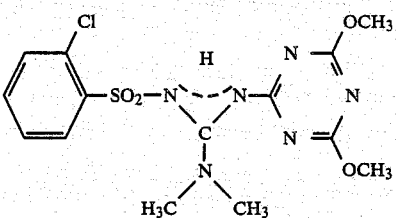

(Process c)
4.5 g (0.1 mol) of dimethylamine are passed into a mixture of 15 g (0.037 mol) of N'-(4,6-dimethoxy-s-triazin-2-yl)-N'''-(2-chloro-benzenesulphonyl)-S-methylisothiourea and 100 ml of dioxane at 25° C. to 35° C. The reaction mixture is then stirred for one hour at 80° C. After the reaction mixture has cooled, the product, which is obtained in crystalline form, is isolated by filtering it off under suction.

12.1 g (73% of theory) of the dimethyl-ammonium salt of N'-(4,6-dimethoxy-s-triazin-2-yl)-N'',N'''-dimethyl-N'''-(2-chloro-benzenesulphonyl)-guanidine (10a) of melting point 162° C. are obtained.

The ammonium salt (10a) is dissolved in 20 ml of water, and the solution is acidified with concentrated hydrochloric acid. The product obtained in crystalline form in this procedure is isolated by filtering it off under suction.

4 g (28% of theory) of N'-(4,6-dimethoxy-s-triazin-2-yl)-N'',N'''-dimethyl-N'''-(2-chlorobenzenesulphonyl)-guanidine (10b) of melting point 185° C. are obtained.

EXAMPLE 11

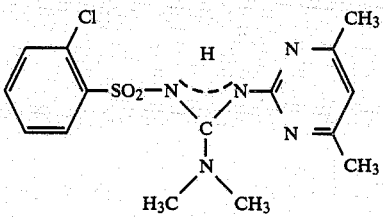

(Process d)
A mixture of 5.5 g (0.01 mol) of N'-(4,6-dimethyl-pyrimidin-2-yl)-N''-methoxy-N'',N'''-bis-(2-chlorobenzenesulphonyl)-guanidine (4), 1.5 g (0.025 mole) of N,N-dimethylhydrazine, 20 ml of ethanol and 10 ml of water is heated at the boil under reflux for 15 minutes. After the mixture has cooled, the product, which is obtained in crystalline form, is isolated by filtering it off under suction.

2.5 g (65% of theory) of N'-(4,6-dimethylpyrimidin-2-yl)-N''-dimethylamino-N'''-(2-chloro-benzenesulphonyl)-guanidine of melting point 176° C. are obtained.

EXAMPLE 12

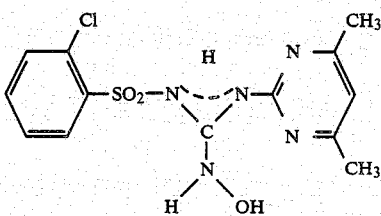

(Process d) po A mixture of 5.5 g (0.01 mol) of N'-(4,6-dimethylpyrimidin-2-yl)-N''-methoxy-N'',N''''-bis-(2-chlorobenzenesulphonyl)-guanidine (4), 2.1 g of hydroxylamine hydrochloride (0.03 mol), 30 ml of ethanol and 5 ml of water, as well as 3.0 g (0.03 mol) of triethylamine, are stirred for 6 hours at 20° C. The product, which is obtained in crystalline form, is isolated by filtering it off under suction.

2.7 g (76% of theory) of N'-(4,6-dimethylpyrimidin-2-yl)-N''-hydroxy-N'''-(2-chloro-benzenesulphonyl)-guanidine of melting point 139° C. are obtained.

EXAMPLE 13

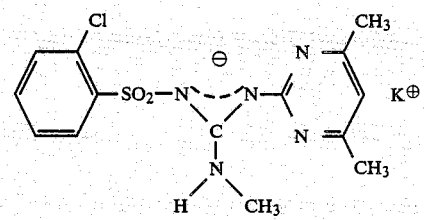

(Process e)
A solution of 0.9 g (0.01 mol) of potassium ethylate in 15 ml of ethanol is added to a mixture of 3.5 g (0.01 mol) of N'-(4,6-dimethyl-pyrimidin-2-yl)-N''-methyl-N'''-(2-chloro-benzenesulphonyl)-guanidine and 15 ml of ethanol, and the reaction mixture is stirred for hours at 20° C. The product, which is obtained in crystalline form, is isolated by filtering it off under suction.

3.8 g (96% of theory) of the potassium salt of N'-(4,6-dimethyl-pyrimidin-2-yl)-N''-methyl-N'''-(2-chloro-benzenesulphonyl)-guanidine of melting point 290° C. are obtained.

EXAMPLE 14

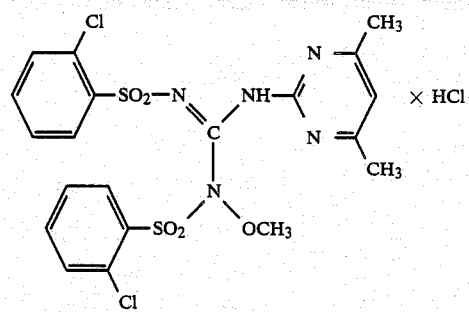

(Process f)
5 ml of concentrated hydrochloric acid (0.05 mol) are added to a mixture of 5.5 g (0.01 mol) of N'-(4,6-dimethylpyrimidin-2-yl)-N'''-methoxy-N'',N''''-bis-(2-chlorobenzenesulphonyl)-guanidine and 25 ml of acetic anhydride at 20° C. (exothermic reaction!), and the reaction mixture is stirred for 2 hours. The product, which is obtained in crystalline form, is isolated by filtering it off under suction.

4.3 g (74% of theory) of N'-(4,6-dimethylpyrimidin-2-yl)-N'''-methoxy-N'',N''''-bis-(2-chlorobenzenesulphonyl)-guanidine hydrochloride of melting point 142° C. are obtained.

EXAMPLE 15

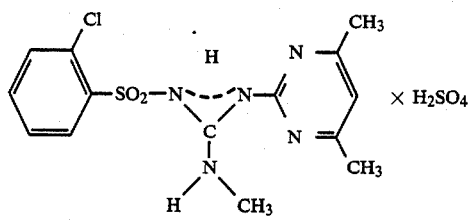

(Process f)

A mixture of 3.5 g (0.01 mol) of N'-(4,6-dimethylpyrimidin-2-yl)-N'''-methyl-N''''-(2-chloro-benzenesulphonyl)-guanidine, 25 ml of isopropanol and 4.9 g (0.05 mol) of concentrated sulphuric acid is stirred for 6 hours at 20° C. The product, which is obtained in crystalline form, is isolated by filtering it off under suction.

3.1 g (64% of theory) of N'-(4,6-dimethyl-pyrimidin-2-yl)-N'''-methyl-N''''-(2-chloro-benzenesulphonyl)-guanidine dihydrogen sulphate of melting point 162° C. are obtained.

It was possible to prepare the compounds of the formula (I) listed in the table below by the processes described, by way of example, in the examples above.

TABLE 1

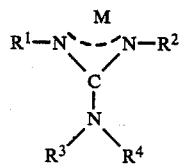

| Example No. | $R^1$ | $R^2$ | $R^3$ | $R^4$ | M | Melting point (°C.) |
|---|---|---|---|---|---|---|
| 16 | H | ![4,6-dimethylpyrimidin-2-yl] | H | $-OC_2H_5$ | H | 66 |
| 17 | H | ![4,6-dimethylpyrimidin-2-yl] | H | $-OCH_2$-phenyl | H | 77 |
| 18 | H | ![4,6-dimethoxy-1,3,5-triazin-2-yl] | H | phenyl | H | |
| 19 | H | ![4,6-dimethylpyrimidin-2-yl] | H | $-CH_3$ | H | 240 |

TABLE 1-continued
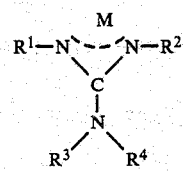
(I)
| Example No. | R¹ | R² | R³ | R⁴ | M | Melting point (°C.) |
|---|---|---|---|---|---|---|
| 20 | H | (pyrimidinyl-4,6-diCH₃) | H | —C₂H₅ | H | 184 |
| 21 | H | (pyrimidinyl-4,6-diCH₃) | H | —CH(CH₃)₂ | H | 213 |
| 22 | H | (pyrimidinyl-4,6-diCH₃) | H | H | H | 240 |
| 23 | H | (pyrimidinyl-4,6-diCH₃) | n-C₄H₉ | n-C₄H₉ | H | 88 |
| 24 | H | (pyrimidinyl-4,6-diCH₃) | H | —CH₂—C₆H₅ | H | 197 |
| 25 | H | (pyrimidinyl-4,6-diCH₃) | H | —N(CH₃)₂ | H | 149 |
| 26 | H | (pyrimidinyl-4,6-diCH₃) | H | —C₆H₅ | H | 207 |

TABLE 1-continued
$$R^1-N\underset{\underset{\underset{R^4}{R^3}}{\overset{|}{N}}}{\overset{M}{\underset{\|}{C}}}N-R^2 \quad (I)$$
| Example No. | R¹ | R² | R³ | R⁴ | M | Melting point (°C.) |
|---|---|---|---|---|---|---|
| 27 | H | 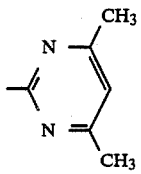 | H | 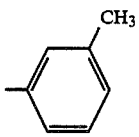 | H | 182 |
| 28 | H | 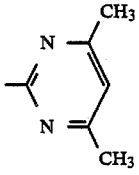 | H | 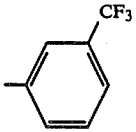 | H | 138 |
| 29 | H | 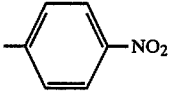 | H | 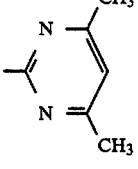 | H | 232 |
| 30 | H | 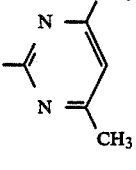 | CH₃ |  | H | 197 |
| 31 | H | 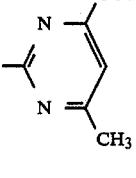 | H |  | —CH₃ | 208 |
| 32 | H |  | H | 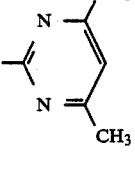 | H | 205 |
| 33 | H | 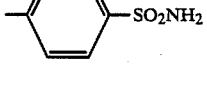 | H | 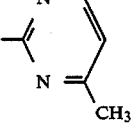 | H | |

TABLE 1-continued $$\underset{R^3\ R^4}{\overset{R^1-N\overset{M}{\underset{C}{\diagdown}}N-R^2}{\underset{\underset{N}{|}}{|}}} \quad (I)$$

| Example No. | R¹ | R² | R³ | R⁴ | M | Melting point (°C.) |
|---|---|---|---|---|---|---|
| 34 | H | 2-(4,6-dimethylpyrimidinyl) | H | —OCH₃ | —CH₃ | |
| 35 | 2-Cl-C₆H₄-SO₂— | 2-(4,6-dimethylpyrimidinyl) | H | C₆H₅ | H | 196 |
| 36 | 2-CH₃-C₆H₄-SO₂— | 2-(4,6-dimethylpyrimidinyl) | H | C₆H₅ | H | |
| 37 | 2-(COOCH₃)-C₆H₄-SO₂— | 2-(4,6-dimethylpyrimidinyl) | H | C₆H₅ | H | |
| 38 | 2-(CF₃)-C₆H₄-SO₂— | 2-(4,6-dimethylpyrimidinyl) | H | C₆H₅ | H | |
| 39 | 2-(NO₂)-C₆H₄-SO₂— | 2-(4,6-dimethylpyrimidinyl) | H | C₆H₅ | H | |
| 40 | 2-Cl-C₆H₄-SO₂— | 2-(4,6-dimethylpyrimidinyl) | H | 4-Cl-C₆H₄ | H | 212 |

TABLE 1-continued

Structure (I):
$R^1-N, N-R^2$ with M bridging, connected to C which bears $N(R^3)(R^4)$

| Example No. | R¹ | R² | R³ | R⁴ | M | Melting point (°C.) |
|---|---|---|---|---|---|---|
| 41 | 2-CH₃-C₆H₄-SO₂— | 4,6-dimethylpyrimidin-2-yl | H | 4-Cl-C₆H₄— | H | 208 |
| 42 | 2-NO₂-C₆H₄-SO₂— | 4,6-dimethylpyrimidin-2-yl | H | 4-Cl-C₆H₄— | H | 255 |
| 43 | H | 4,6-dimethylpyrimidin-2-yl | 2-NO₂-C₆H₄-SO₂— | 4-Cl-C₆H₄— | H | 103 |
| 44 | 2-CF₃-C₆H₄-SO₂— | 4,6-dimethylpyrimidin-2-yl | H | 4-Cl-C₆H₄— | H | 212 |
| 45 | 2-(COOCH₃)-C₆H₄-SO₂— | 4,6-dimethylpyrimidin-2-yl | H | 4-Cl-C₆H₄— | H | 248 |
| 46 | 2-Cl-C₆H₄-SO₂— | 4,6-dimethylpyrimidin-2-yl | H | 3-CH₃-C₆H₄— | H | 178 |
| 47 | 2-NO₂-C₆H₄-SO₂— | 4,6-dimethylpyrimidin-2-yl | H | 3-CH₃-C₆H₄— | H | 231 |

TABLE 1-continued $$R^1-N\underset{\underset{R^3}{\overset{|}{N}}R^4}{\overset{M}{\underset{C}{\cdots}}}N-R^2 \quad (I)$$

| Example No. | R¹ | R² | R³ | R⁴ | M | Melting point (°C.) |
|---|---|---|---|---|---|---|
| 48 | 2-CH₃-C₆H₄-SO₂— | 4,6-dimethylpyrimidin-2-yl | H | 3-methylphenyl | H | 165 |
| 49 | 2-CF₃-C₆H₄-SO₂— | 4,6-dimethylpyrimidin-2-yl | H | 3-methylphenyl | H | 188 |
| 50 | 2-Cl-C₆H₄-SO₂— | 4,6-dimethylpyrimidin-2-yl | H | —CH₂-C₆H₅ | H | 139 |
| 51 | 2-CH₃-C₆H₄-SO₂— | 4,6-dimethylpyrimidin-2-yl | H | —CH₂-C₆H₅ | H | 139 |
| 52 | 2-NO₂-C₆H₄-SO₂— | 4,6-dimethylpyrimidin-2-yl | H | —CH₂-C₆H₅ | H | 191 |
| 53 | H | 4,6-dimethylpyrimidin-2-yl | 2-NO₂-C₆H₄-SO₂— | —CH₂-C₆H₅ | H | 168 |
| 54 | 2-COOCH₃-C₆H₄-SO₂— | 4,6-dimethylpyrimidin-2-yl | H | —CH₂-C₆H₅ | H | 150 |

TABLE 1-continued $$R^1-N\overset{M}{\underset{\underset{R^3}{\underset{|}{N}}\underset{R^4}{}}{\overset{|}{C}}}N-R^2 \quad (I)$$

| Example No. | R¹ | R² | R³ | R⁴ | M | Melting point (°C.) |
|---|---|---|---|---|---|---|
| 55 | 2-Cl-C₆H₄-SO₂- | 4,6-dimethylpyrimidin-2-yl | H | n-C₄H₉ | H | 103 |
| 56 | 2-(COOCH₃)-C₆H₄-SO₂- | 4,6-dimethylpyrimidin-2-yl | H | n-C₄H₉ | H | |
| 57 | 2-Cl-C₆H₄-SO₂- | 4,6-dimethylpyrimidin-2-yl | -C₄H₉n | n-C₄H₉ | H | 150 |
| 58 | 2-Cl-C₆H₄-SO₂- | 4,6-dimethylpyrimidin-2-yl | H | -C₂H₅ | H | 112 |
| 59 | 2-Cl-C₆H₄-SO₂- | 4,6-dimethylpyrimidin-2-yl | H | -CH₃ | H | 160 |
| 60 | 2-Cl-C₆H₄-SO₂- | 4,6-dimethylpyrimidin-2-yl | -CH₃ | C₆H₅- | H | 200 |
| 61 | 2-CH₃-C₆H₄-SO₂- | 4,6-dimethylpyrimidin-2-yl | -CH₃ | C₆H₅- | H | 171 |

TABLE 1-continued $$\begin{array}{c} M \\ | \\ R^1-N-C-N-R^2 \\ | \\ N \\ / \ \backslash \\ R^3 \ R^4 \end{array} \quad (I)$$

| Example No. | R¹ | R² | R³ | R⁴ | M | Melting point (°C.) |
|---|---|---|---|---|---|---|
| 62 | 2-Cl-C₆H₄-SO₂— | 4,6-(CH₃)₂-pyrimidin-2-yl | H | 3-CF₃-C₆H₄— | H | 185 |
| 63 | H | 4,6-(CH₃)₂-pyrimidin-2-yl | 2-Cl-C₆H₄-SO₂— | 3-CF₃-C₆H₄— | H | 221 |
| 64 | 2-CH₃-C₆H₄-SO₂— | 4,6-(CH₃)₂-pyrimidin-2-yl | H | 3-CF₃-C₆H₄— | H | 235 |
| 65 | 2-NO₂-C₆H₄-SO₂— | 4,6-(CH₃)₂-pyrimidin-2-yl | H | 3-CF₃-C₆H₄— | H | 162 |
| 66 | 2,5-Cl₂-C₆H₃-SO₂— | 4,6-(CH₃)₂-pyrimidin-2-yl | H | 3-CF₃-C₆H₄— | H | 204 |
| 67 | 2-Cl-C₆H₄-SO₂— | 4,6-(CH₃)₂-pyrimidin-2-yl | H | 4-NO₂-C₆H₄— | H | 220 |
| 68 | 2-CH₃-C₆H₄-SO₂— | 4,6-(CH₃)₂-pyrimidin-2-yl | H | 4-NO₂-C₆H₄— | H | 218 |

TABLE 1-continued

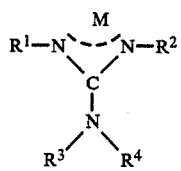
(I)

| Example No. | R¹ | R² | R³ | R⁴ | M | Melting point (°C.) |
|---|---|---|---|---|---|---|
| 69 | 2-Cl-C₆H₄-SO₂— | 4,6-dimethylpyrimidin-2-yl | H | tetrahydrothiophene-3-yl-SO₂ | H | |
| 70 | 2-Cl-C₆H₄-SO₂— | 4,6-dimethoxy-1,3,5-triazin-2-yl | H | —CH(CH₃)₂ | H | 97 |
| 71 | H | 4,6-dimethylpyrimidin-2-yl | 2-CH₃-C₆H₄-SO₂— | —OCH₃ | H | 91 |
| 72 | 3-Cl-C₆H₄-SO₂— | 4,6-dimethylpyrimidin-2-yl | 3-Cl-C₆H₄-SO₂— | —OCH₃ | H | 154 |
| 73 | C₆H₅-SO₂— | 4,6-dimethylpyrimidin-2-yl | C₆H₅-SO₂— | —OCH₃ | H | 149 |
| 74 | 2,5-Cl₂-C₆H₃-SO₂— | 4,6-dimethylpyrimidin-2-yl | 2-Cl-C₆H₄-SO₂— | —OCH₃ | H | 142 |
| 75 | 2-CH₃-5-Cl-C₆H₃-SO₂— | 4,6-dimethylpyrimidin-2-yl | 2-CH₃-5-Cl-C₆H₃-SO₂— | —OCH₃ | H | 135 |

TABLE 1-continued

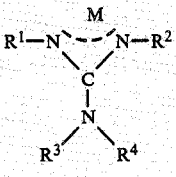
(I)

| Example No. | R¹ | R² | R³ | R⁴ | M | Melting point (°C.) |
|---|---|---|---|---|---|---|
| 76 | 2-COOCH₃-C₆H₄-SO₂— | 4,6-dimethylpyrimidin-2-yl | 2-COOCH₃-C₆H₄-SO₂— | —OC₂H₅ | H | 129 |
| 77 | 2-Cl-C₆H₄-SO₂— | 4,6-dimethylpyrimidin-2-yl | 2-Cl-C₆H₄-SO₂— | —OC₂H₅ | H | 170 |
| 78 | 2-CH₃-C₆H₄-SO₂— | 4,6-dimethylpyrimidin-2-yl | 2-CH₃-C₆H₄-SO₂— | —OCH₃ | H | 129 |
| 79 | 2-biphenyl-SO₂— | 4,6-dimethylpyrimidin-2-yl | 2-biphenyl-SO₂— | —OCH₃ | H | 171 |
| 80 | 2-biphenyl-SO₂— | 4,6-dimethylpyrimidin-2-yl | 2-biphenyl-SO₂— | —OC₂H₅ | H | 174 |
| 81 | 2,5-diCl-C₆H₃-SO₂— | 4,6-dimethylpyrimidin-2-yl | 2,5-diCl-C₆H₃-SO₂— | —OC₂H₅ | H | 158 |
| 82 | 2-NO₂-C₆H₄-S— | 4,6-dimethylpyrimidin-2-yl | 2-NO₂-C₆H₄-S— | —OCH₃ | H | 150 |

TABLE 1-continued
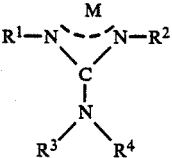
(I)
| Example No. | R¹ | R² | R³ | R⁴ | M | Melting point (°C.) |
|---|---|---|---|---|---|---|
| 83 | 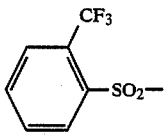 | 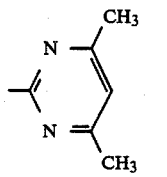 | 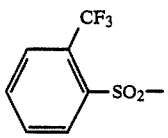 | —OCH₃ | H | 121 |
| 84 | 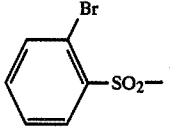 | 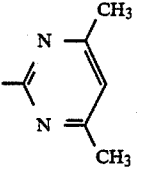 | 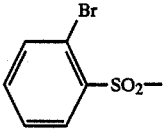 | —OCH₃ | H | 147 |
| 85 | 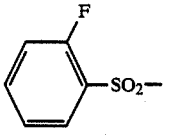 | 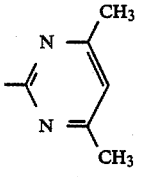 | 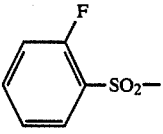 | —OCH₃ | H | 166 |
| 86 | 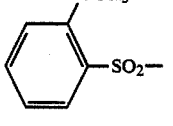 | 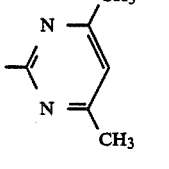 | 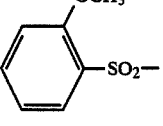 | —OCH₃ | H | 196 |
| 87 | 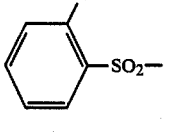 | 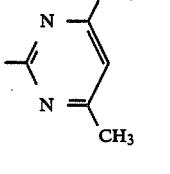 | 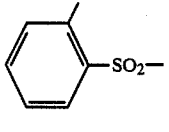 | —OCH₂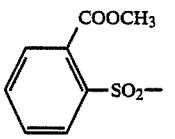 | H | 175 |
| 88 | 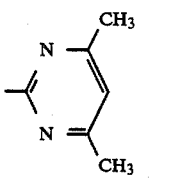 | 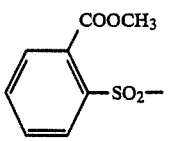 | 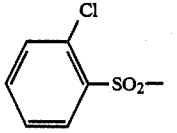 | —OCH₂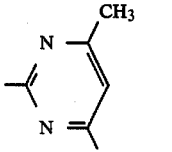 | H | 85 |
| 89 | Cl<br>—SO₂— | N=C(CH₃)—CH=C(CH₃)—N | H | —CH(CH₃)₂ | H | 136 |

TABLE 1-continued $$\begin{array}{c} M \\ | \\ R^1-N\cdots C\cdots N-R^2 \\ | \\ N \\ / \ \backslash \\ R^3 \quad R^4 \end{array} \quad (I)$$

| Example No. | R¹ | R² | R³ | R⁴ | M | Melting point (°C.) |
|---|---|---|---|---|---|---|
| 90 | 2-Cl-C₆H₄-SO₂– | 4,6-dimethylpyrimidin-2-yl | H | H | H | 176 |
| 91 | 2-Cl-C₆H₄-SO₂– | 4,6-dimethylpyrimidin-2-yl | H | –CH₂CH(CH₃)₂ | H | 105 |
| 92 | 2-Cl-C₆H₄-SO₂– | 4,6-dimethylpyrimidin-2-yl | H | –CH₂CH₂Cl | H | 152 |
| 93 | 2-Cl-C₆H₄-SO₂– | 4,6-dimethylpyrimidin-2-yl | H | 2-methylphenyl | H | 225 |
| 94 | C₆H₅-SO₂– | 4,6-dimethylpyrimidin-2-yl | H | H | H | 167 |
| 95 | C₆H₅-SO₂– | 4,6-dimethylpyrimidin-2-yl | H | –C₂H₅ | H | 143 |
| 96 | 2-Cl-C₆H₄-SO₂– | 4,6-dimethylpyrimidin-2-yl | H | –CH₂COOC₂H₅ | H | 123 |

TABLE 1-continued $$R^1-N\overset{M}{\underset{\underset{\underset{R^4}{N}}{|}}{-}}N-R^2$$
(I)

| Example No. | R¹ | R² | R³ | R⁴ | M | Melting point (°C.) |
|---|---|---|---|---|---|---|
| 97 | 2-Cl-C₆H₄-SO₂- | 4,6-dimethylpyrimidin-2-yl | H | -CH₂-CH=CH₂ | H | 108 |
| 98 | 2-Cl-C₆H₄-SO₂- | 4,6-dimethylpyrimidin-2-yl | -CH₃ | -CH₃ | H | 160 |
| 99 | 2-COOCH₃-C₆H₄-SO₂- | 4,6-dimethylpyrimidin-2-yl | -CH(CH₃)₂ | -CH(CH₃)₂ | H | 189 |
| 100 | 2-Cl-C₆H₄-SO₂- | 4,6-dimethylpyrimidin-2-yl | -CH(CH₃)₂ | -CH(CH₃)₂ | H | 88 |
| 101 | 2-Cl-C₆H₄-SO₂- | 4,6-dimethylpyrimidin-2-yl | cyclohexyl | cyclohexyl | H | 122 |
| 102 | 3-Cl-C₆H₄-SO₂- | 4,6-dimethylpyrimidin-2-yl | H | -C(CH₃)₃ | H | 113 |
| 103 | 2-Cl-C₆H₄-SO₂- | 4,6-dimethylpyrimidin-2-yl | H | -OCH₃ | H | 142 |

TABLE 1-continued $$R^1-N\overset{M}{\underset{\underset{R^3\ R^4}{|}}{\underset{C}{-}}}N-R^2 \quad (I)$$

| Example No. | R¹ | R² | R³ | R⁴ | M | Melting point (°C.) |
|---|---|---|---|---|---|---|
| 104 | 2-CH₃-C₆H₄-SO₂— | 4,6-(CH₃)₂-pyrimidin-2-yl | H | —CH₃ | H | 157 |
| 105 | 2-Cl-C₆H₄-SO₂— | 4,6-(CH₃)₂-pyrimidin-2-yl | H | cyclohexyl | H | 162 |
| 106 | 2-Cl-C₆H₄-SO₂— | 4,6-(CH₃)₂-pyrimidin-2-yl | H | —CH₂CH₂OH | H | 84 |
| 107 | 2-COOCH₃-C₆H₄-SO₂— | 4,6-(CH₃)₂-pyrimidin-2-yl | H | —N(CH₃)₂ | H | 150 |
| 108 | 2-COOCH₃-C₆H₄-SO₂— | 4,6-(CH₃)₂-pyrimidin-2-yl | H | —CH₃ | H | 134 |
| 109 | 2-COOCH₃-C₆H₄-SO₂— | 4,6-(CH₃)₂-pyrimidin-2-yl | H | —OCH₃ | H | 132 |
| 110 | 2-Cl-C₆H₄-SO₂— | 4,6-(CH₃)₂-pyrimidin-2-yl | H | —C₃H₇n | H | 100 |

TABLE 1-continued $$R^1-N\overset{M}{\underset{\underset{\underset{R^4}{N}}{C}}{\cdots}}N-R^2 \quad (I)$$

| Example No. | R¹ | R² | R³ | R⁴ | M | Melting point (°C.) |
|---|---|---|---|---|---|---|
| 111 | 2-Cl-C₆H₄-SO₂- | 4,6-dimethylpyrimidin-2-yl | -C₂H₅ | -C₂H₅ | H | 134 |
| 112 | 2-(COOCH₃)-C₆H₄-SO₂- | 4,6-dimethylpyrimidin-2-yl | H | -CH₂CH₂OH | H | 136 |
| 113 | 2-CH₃-C₆H₄-SO₂- | 4,6-dimethylpyrimidin-2-yl | -C₂H₅ | -C₂H₅ | H | 145 |
| 114 | 2-Cl-C₆H₄-SO₂- | 4,6-dimethylpyrimidin-2-yl | H | 2-H₂N-C₆H₄- | H | 171 |
| 115 | 2-Cl-C₆H₄-SO₂- | 4,6-dimethylpyrimidin-2-yl | H | -CH₂-CH₂-OCH₃ | H | 118 |
| 116 | 2-CH₃-C₆H₄-SO₂- | 4,6-dimethylpyrimidin-2-yl | H | -N(CH₃)₂ | H | 128 |
| 117 | 2-Cl-C₆H₄-SO₂- | 4,6-dimethylpyrimidin-2-yl | H | -NHCOCH₃ | H | 185 |

TABLE 1-continued $$\begin{array}{c} M \\ R^1-N \diagdown \diagup N-R^2 \\ C \\ | \\ N \\ R^3 \diagup \diagdown R^4 \end{array} \quad (I)$$

| Example No. | R¹ | R² | R³ | R⁴ | M | Melting point (°C.) |
|---|---|---|---|---|---|---|
| 118 | 2-CH₃-C₆H₄-SO₂- | 4,6-dimethylpyrimidin-2-yl | H | —NHCOCH₃ | H | 143 |
| 119 | 2-COOCH₃-C₆H₄-SO₂- | 4,6-dimethylpyrimidin-2-yl | H | —NHCOCH₃ | H | 150 |
| 120 | 2-Cl-C₆H₄-SO₂- | 4,6-dimethylpyrimidin-2-yl | —CH₂CH₂—O—CH₂CH₂— | | H | 192 |
| 121 | 2-CH₃-C₆H₄-SO₂- | 4,6-dimethylpyrimidin-2-yl | H | —OCH₃ | H | 114 |
| 122 | 2-Cl-C₆H₄-SO₂- | 4,6-dimethylpyrimidin-2-yl | H | —NHCOOCH₃ | H | 187 |
| 123 | 2-Cl-C₆H₄-SO₂- | 4,6-dimethylpyrimidin-2-yl | H | —NH—SO₂—C₆H₄—CH₃ | H | 203 |
| 124 | 2-Cl-C₆H₄-SO₂- | 4,6-dimethylpyrimidin-2-yl | H | —NH—(tetrahydrothiophene-1,1-dioxide-3-yl) | H | 153 |

TABLE 1-continued $$R^1-N\overset{M}{\underset{\underset{R^3}{\underset{|}{N}}-R^4}{\cdots}}\overset{\cdots}{\underset{C}{\cdots}}N-R^2$$ (I)

| Example No. | R¹ | R² | R³ | R⁴ | M | Melting point (°C.) |
|---|---|---|---|---|---|---|
| 125 | 2-Br-C₆H₄-SO₂- | 4,6-dimethylpyrimidin-2-yl | H | -OCH₃ | H | 166 |
| 126 | 2-F-C₆H₄-SO₂- | 4,6-dimethylpyrimidin-2-yl | H | -OCH₃ | H | 160 |
| 127 | 2-Cl-C₆H₄-SO₂- | 4,6-dimethylpyrimidin-2-yl | H | -NH-(pyrimidin-2-yl) | H | 210 |
| 128 | 2-Cl-C₆H₄-SO₂- | 4,6-dimethylpyrimidin-2-yl | H | -N(morpholino) | H | 188 |
| 129 | 2-Cl-C₆H₄-SO₂- | 4,6-dimethylpyrimidin-2-yl | -CH₂-CH₂-N(COCH₃)-CH₂-CH₂- | | H | 100 |
| 130 | 2-Cl-C₆H₄-SO₂- | 4,6-dimethylpyrimidin-2-yl | 2-Cl-C₆H₄-SO₂- | -OCH₃ | Na | 182 |
| 131 | 2-Cl-C₆H₄-SO₂- | 4,6-dimethylpyrimidin-2-yl | 2-Cl-C₆H₄-SO₂- | -OCH₃ | K | 165 |

TABLE 1-continued $$\begin{array}{c} M \\ R^1-N\cdots N-R^2 \\ C \\ | \\ N \\ R^3\ R^4 \end{array} \quad (I)$$

| Example No. | R¹ | R² | R³ | R⁴ | M | Melting point (°C.) |
|---|---|---|---|---|---|---|
| 132 | 2-Cl-C₆H₄-SO₂— | 4,6-dimethylpyrimidin-2-yl | 2-Cl-C₆H₄-SO₂— | —OCH₃ | ½ Ca | 165 |
| 133 | 2-Cl-C₆H₄-SO₂— | 4,6-dimethylpyrimidin-2-yl | —CH₃ | —OH | H | 161 |
| 134 | 2-Cl-C₆H₄-SO₂— | 4,6-dimethylpyrimidin-2-yl | H | 4,5-dihydrooxazol-2-yl | H | 121 |
| 135 | H | 4,6-dimethylpyrimidin-2-yl | H | 4-OCH₃-C₆H₄— | H | 179 |
| 136 | H | 4,6-dimethylpyrimidin-2-yl | H | 4-CF₃-C₆H₄— | H | 171 |
| 137 | 2-Cl-C₆H₄-SO₂— | 4,6-dimethoxypyrimidin-2-yl | H | i-C₃H₇ | H | 185 |
| 138 | 2-Cl-C₆H₄-SO₂— | 4,6-dimethylpyrimidin-2-yl | H | n-C₄H₉ | H | 103 |

TABLE 1-continued $$R^1-N\underset{\underset{R^3\quad R^4}{N}}{\overset{M}{\underset{C}{\|}}}N-R^2 \qquad (I)$$

| Example No. | R¹ | R² | R³ | R⁴ | M | Melting point (°C.) |
|---|---|---|---|---|---|---|
| 139 | H | 4,6-dimethylpyrimidin-2-yl | 2-chlorophenylsulfonyl | —OCH₃ | H | 90 |
| 140 | 2-(methoxycarbonyl)phenylsulfonyl | 4,6-dimethylpyrimidin-2-yl | H | 3-methylphenyl | H | 170 |
| 141 | 2-chlorophenylsulfonyl | 4-methoxy-6-methylpyrimidin-2-yl | H | phenyl | CH₃ | 204 |
| 142 | 2-biphenylsulfonyl | 4,6-dimethylpyrimidin-2-yl | H | 4-nitrophenyl | H | 135 |
| 143 | 2-methylphenylsulfonyl | 4-methyl-6-methoxypyrimidin-2-yl | H | —CH₂—CH=CH₂ | H | 117 |
| 144 | 2-methylphenylsulfonyl | 4-methyl-6-methoxypyrimidin-2-yl | H | CH₃ | H | 153 |
| 145 | 2-methylphenylsulfonyl | 4-methyl-6-methoxypyrimidin-2-yl | H | i-C₃H₇ | H | 108 |

TABLE 1-continued
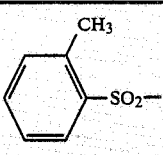
(I)
| Example No. | R¹ | R² | R³ | R⁴ | M | Melting point (°C.) |
|---|---|---|---|---|---|---|
| 146 | 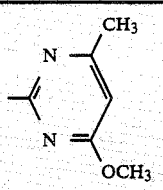 |  | H | —N(CH₃)₂ | H | 140 |
| 147 | H | 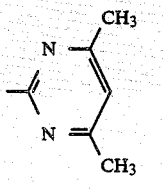 | 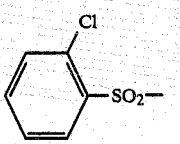 | —OCH₃ | H | 90 |
| 148 |  | 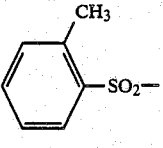 | 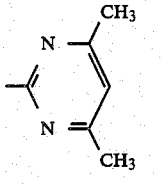 | —OC₂H₅ | H | 139 |
| 149 | 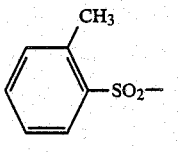 |  | H | 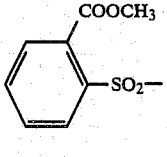 | H | 205 |
| 150 | 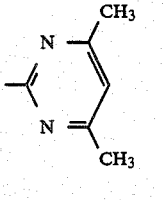 | 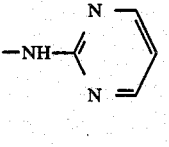 | H | —NHCOOCH₃ | H | 142 |
| 151 | 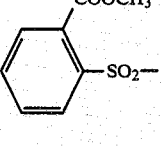 | 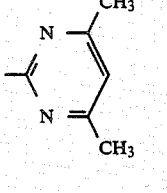 | H | 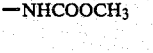 | H | 251 |
| 152 | 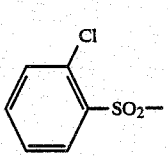 | 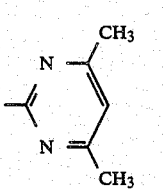 | H | —CH₂—CH(OCH₃)₂ | H | 129 |

TABLE 1-continued $$\begin{array}{c} M \\ R^1-N\diagdown \diagup N-R^2 \\ C \\ | \\ N \\ \diagup \diagdown \\ R^3 \quad R^4 \end{array} \quad (I)$$

| Example No. | R¹ | R² | R³ | R⁴ | M | Melting point (°C.) |
|---|---|---|---|---|---|---|
| 153 | 2-Cl-5-NO₂-C₆H₃-SO₂— | 4,6-dimethylpyrimidin-2-yl | H | —OCH₃ | H | 163 |
| 154 | 2-(COOCH₃)-C₆H₄-SO₂— | 4,6-dimethylpyrimidin-2-yl | 2-(COOCH₃)-C₆H₄-SO₂— | —OCH₃ | K | 170 |
| 155 | 2-(COOCH₃)-C₆H₄-SO₂— | 4,6-dimethylpyrimidin-2-yl | H | H | H | 135 |
| 156 | 2-(COOCH₃)-C₆H₄-SO₂— | 4,6-dimethylpyrimidin-2-yl | CH₃ | CH₃ | H | 136 |
| 157 | 2-(COOCH₃)-C₆H₄-SO₂— | 4,6-dimethylpyrimidin-2-yl | 2-(COOCH₃)-C₆H₄-SO₂— | —OCH₂CH₂CH₃ | H | 110 |
| 158 | 2-(COOCH₃)-C₆H₄-SO₂— | 5-bromo-4,6-dimethylpyrimidin-2-yl | 2-(COOCH₃)-C₆H₄-SO₂— | —OCH₃ | H | 112 |
| 159 | 2-Cl-5-CF₃-C₆H₃-SO₂— | 4,6-dimethylpyrimidin-2-yl | H | —OCH₃ | H | 135 |

TABLE 1-continued $$\begin{array}{c} M \\ | \\ R^1-N\cdots C\cdots N-R^2 \\ | \\ N \\ / \ \backslash \\ R^3 \ \ R^4 \end{array} \quad (I)$$

| Example No. | R¹ | R² | R³ | R⁴ | M | Melting point (°C.) |
|---|---|---|---|---|---|---|
| 160 | 2-(COOC₂H₅)C₆H₄-SO₂— | 4,6-dimethylpyrimidin-2-yl | H | —OCH₃ | H | 126 |
| 161 | 2-(COOCH₃)C₆H₄-SO₂— | 4,6-dimethylpyrimidin-2-yl | 3-Cl-C₆H₄-SO₂— | —OCH₃ | H | 159 |
| 162 | 2-Cl-C₆H₄-SO₂— | 4,6-dimethylpyrimidin-2-yl | H | —NH-C₆H₅ | H | 118 |
| 163 | 2-(COOCH₃)C₆H₄-SO₂— | 4,6-dimethylpyrimidin-2-yl | 4-CH₃-C₆H₄-SO₂— | —OCH₃ | H | 150 |
| 164 | 2-Cl-C₆H₄-SO₂— | 5-Br-4,6-dimethylpyrimidin-2-yl | 2-Cl-C₆H₄-SO₂— | —OCH₃ | H | 157 |
| 165 | 2-(COOCH₃)C₆H₄-SO₂— | 4,6-dimethylpyrimidin-2-yl | 2-Cl-C₆H₄-SO₂— | —OCH₃ | H | 150 |
| 166 | 2-CH₃-C₆H₄-SO₂— | 4,6-dimethylpyrimidin-2-yl | H | —C₄H₉—n | H | 90 |

TABLE 1-continued $$R^1-N\overset{M}{\underset{\underset{\underset{R^3}{N}}{C}}{}}N-R^2 \quad (I)$$
$$\phantom{R^1-N}\underset{R^3\phantom{NN}R^4}{}$$

| Example No. | R¹ | R² | R³ | R⁴ | M | Melting point (°C.) |
|---|---|---|---|---|---|---|
| 167 | H | 4,6-dimethylpyrimidin-2-yl | H | phenyl | CH₃ | 267 |
| 168 | 2-Cl-C₆H₄-SO₂— | 4,6-dimethylpyrimidin-2-yl | H | 4-OCH₃-C₆H₄— | H | 205 |
| 169 | 2-Cl-C₆H₄-SO₂— | 4,6-dimethylpyrimidin-2-yl | 2-Cl-C₆H₄-SO₂— | 4-OCH₃-C₆H₄— | H | 95 |
| 170 | 2-Cl-C₆H₄-SO₂— | 4,6-dimethoxy-1,3,5-triazin-2-yl | H | H | H | |
| 171 | 2-Cl-C₆H₄-SO₂— | 4-CH₃-6-OCH₃-pyrimidin-2-yl | H | —OCH₃ | H | 138 |
| 172 | 2-Cl-C₆H₄-SO₂— | 4-CH₃-6-OCH₃-pyrimidin-2-yl | H | —N(CH₃)₂ | H | 169 |
| 173 | 2-Cl-C₆H₄-SO₂— | 4-CH₃-6-OCH₃-pyrimidin-2-yl | H | H | H | 155 |

TABLE 1-continued $$\begin{array}{c} M \\ R^1-N\phantom{-}N-R^2 \\ \diagdown\phantom{-}\diagup \\ C \\ | \\ N \\ \diagup\phantom{-}\diagdown \\ R^3\phantom{--}R^4 \end{array} \quad (I)$$

| Example No. | R¹ | R² | R³ | R⁴ | M | Melting point (°C.) |
|---|---|---|---|---|---|---|
| 174 | 2-Cl-C₆H₄-SO₂- | 4-CH₃-6-OCH₃-pyrimidin-2-yl | H | CH₃ | H | 153 |
| 175 | 2-CH₃-C₆H₄-SO₂- | 4-CH₃-6-OCH₃-pyrimidin-2-yl | H | -CH₂-C₆H₅ | H | 184 |
| 176 | 2-Cl-C₆H₄-SO₂- | 4-CH₃-6-OCH₃-pyrimidin-2-yl | CH₃ | CH₃ | H | 170 |
| 177 | 2-CH₃-C₆H₄-SO₂- | 4,6-(CH₃)₂-pyridin-2-yl | H | CH₃ | H | 166 |
| 178 | 2-CH₃-C₆H₄-SO₂- | 4,6-(CH₃)₂-pyridin-2-yl | CH₃ | CH₃ | H | 88 |
| 179 | 2-CH₃-C₆H₄-SO₂- | 4,6-(CH₃)₂-pyridin-2-yl | H | -CH₂-CH=CH₂ | H | 115 |
| 180 | 2-CH₃-C₆H₄-SO₂- | 4,6-(CH₃)₂-pyridin-2-yl | H | -CH(CH₃)₂ | H | 75 |

TABLE 1-continued $$R^1-N\underset{\underset{\underset{R^3}{N}}{C}}{\overset{M}{-}}N-R^2 \quad (I)$$
$$\phantom{xxxxxxx}R^3\phantom{x}R^4$$

| Example No. | R¹ | R² | R³ | R⁴ | M | Melting point (°C.) |
|---|---|---|---|---|---|---|
| 181 | 2-methylphenyl-SO₂— | 4,6-dimethylpyridin-2-yl | H | —OCH₃ | H | 91 |
| 182 | 2-methylphenyl-SO₂— | 4,6-dimethylpyridin-2-yl | H | —N(CH₃)₂ | H | 134 |
| 183 | 2-methylphenyl-SO₂— | 4,6-dimethylpyridin-2-yl | H | —CH₂—C₆H₅ | H | 113 |
| 184 | 2-methylphenyl-SO₂— | 4-methyl-6-(dimethylamino)-1,3,5-triazin-2-yl | H | CH₃ | H | 152 |
| 185 | 2-methylphenyl-SO₂— | 4-methyl-6-(dimethylamino)-1,3,5-triazin-2-yl | CH₃ | CH₃ | H | 203 |
| 186 | 2-methylphenyl-SO₂— | 4-methyl-6-(dimethylamino)-1,3,5-triazin-2-yl | H | —CH₂CH=CH₂ | H | 105 |
| 187 | 2-methylphenyl-SO₂— | 4-methyl-6-(dimethylamino)-1,3,5-triazin-2-yl | H | —CH(CH₃)₂ | H | 85 |

TABLE 1-continued

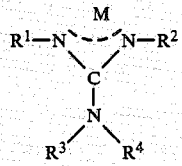

(I)

| Example No. | R¹ | R² | R³ | R⁴ | M | Melting point (°C.) |
|---|---|---|---|---|---|---|
| 188 | 2-CH₃-C₆H₄-SO₂- | 4-CH₃-6-N(CH₃)₂-pyrimidin-2-yl | H | —OCH₃ | H | 105 |
| 189 | 2-CH₃-C₆H₄-SO₂- | 4-CH₃-6-N(CH₃)₂-pyrimidin-2-yl | H | —N(CH₃)₂ | H | 108 |
| 190 | 2-CH₃-C₆H₄-SO₂- | 4-CH₃-6-N(CH₃)₂-pyrimidin-2-yl | H | —CH₂—C₆H₅ | H | 176 |

EXAMPLE 191

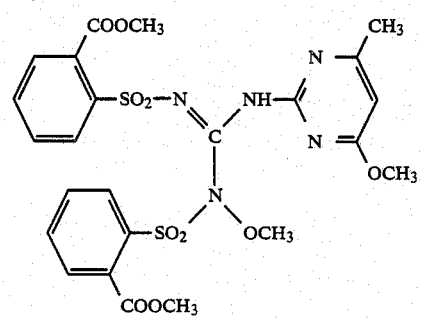

156 g (0.6 mole) of methyl 2-chlorosulfonylbenzoate are added to a mixture of 42 g (0.2 mole) of N,-(4-methoxy-6-methyl-pyrimidine-2-yl)-N″-methoxy-guanidine and 250 ml of pyridine at −20° C., with stirring, and the reaction mixture is stirred then at +20° C. for 2 days. The mixture is then concentrated, the residue is taken up in 1 l of methylene chloride and, after stirring for 30 minutes, acidified with 2N-hydrochloric acid. The organic phase is separated, washed with icy-cold 2N-hydrochloric acid, dried over sodium sulfate and filtered. The filtrate is concentrated, and then 300 ml of ethanol are added, with stirring. After cooling, the product obtained as crystals is isolated by filtration with suction.

Yield: 109 g (90% of theory) of N,-(4-methoxy-6-methyl-pyrimidine-2-yl)-N″-methoxy-N″,N‴,-bis-(2-methoxycarbonyl-phenylsulfonyl)-guanidine of melting point 144° C.

EXAMPLE 192

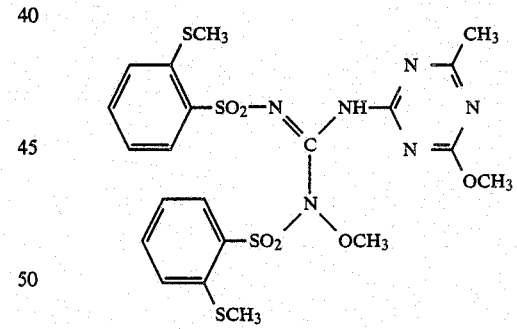

18 g (0.081 mole) of 2-methylthio-benzene-sulfonyl-chloride are added to a mixture of 5.3 g (0.025 mole) of N′-(4-methoxy-6-methyl-1,3,5-triazin-2-yl)-N″-methoxyguanidine, 10 ml of pyridine and 100 ml of methylene chloride at −10° C., with stirring, and then 12 g (0.10 mole) of 1,4-diazabicyclo[2.2] octane are added to this reaction mixture. Stirring is continued at 0° C. for 3 hours and at 20° C. for 15 hours. The resulting solution is washed with 2N-hydrochloric acid, dried over sodium sulfate and filtered. The filtrate is concentrated, and then 30 ml of ethanol are added, with stirring. After cooling, the product obtained as crystals is isolated by filtration with suction.

Yield: 12.7 g (87% of theory of N′-(4-methoxy-6-methyl-1,3,5-triazin-2-yl)-N″-methoxy-N″,N‴-bis-(2- methylthio-phenylsulfonyl)-guanidine of melting point 171° C.

EXAMPLE 193

(alternative method of preparation)

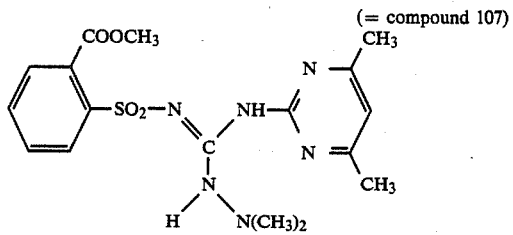

(= compound 107)

A solution of 22.8 g (0.20 mole) of 1,4-diazabicyclolo-[2.2.2] octane in 200 ml of methylene chloride is added dropwise to a mixture of 30 g (0.14 mole) of N'-(4,6-dimethyl-pyrimidine-2-yl)-N"-dimethylamino-guanidine, 39.8 g (0.17 mole) of methyl 2-chlorosulfonylbenzoate and 60 ml of methylene chloride at −10° C., with stirring, and the reaction mixture is stirred then at +20° C. for 4 hours. The resulting solution is then washed with water, dried over sodium sulfate and filtered. The filtrate is concentrated and then 150 ml of isopropanol are added, with stirring. After cooling, the product obtained as crystals is isolated by filtration with suction.

Yield: 49 g (88% of theory) of N'-(4,6-dimethyl-pyrimidine-2-yl)-N"-dimethylamino-N'''-(2-methoxycarbonyl-phenylsulfonyl)-guanidine of melting point 154° C.

A few further derivatives of process (b) according to the invention are described below by way of example:

Preparation of the compound

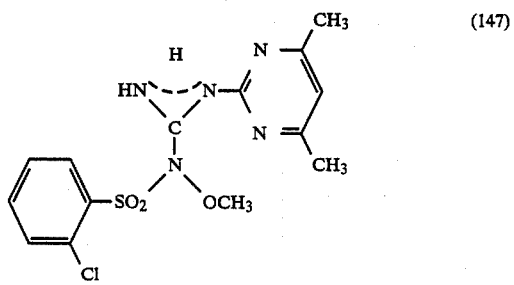

(147)

listed above as EXAMPLE (147).

10.6 g (0.05 mol) of 2-chloro-benzenesulphonyl chloride are added dropwise to a mixture, cooled to −7° C., of 4.9 g (0.025 mol) of N'-(4,6-dimethyl-pyrimidin-2-yl)-N"-methoxy-guanidine and 50 ml of pyridine.

After the reaction mixture has been stirred for minutes at −7° C., 400 ml of water are added to it. The product, which is obtained in crystalline form, is isolated by filtering it off under suction.

5.2 g (56% of theory) of N'-(4,6-dimethylpyrimidin-2-yl)-N"-(2-chloro-benzenesulphonyl)-N"-methoxy-guanidine of melting point 90° C. are obtained.

Preparation of the compounds

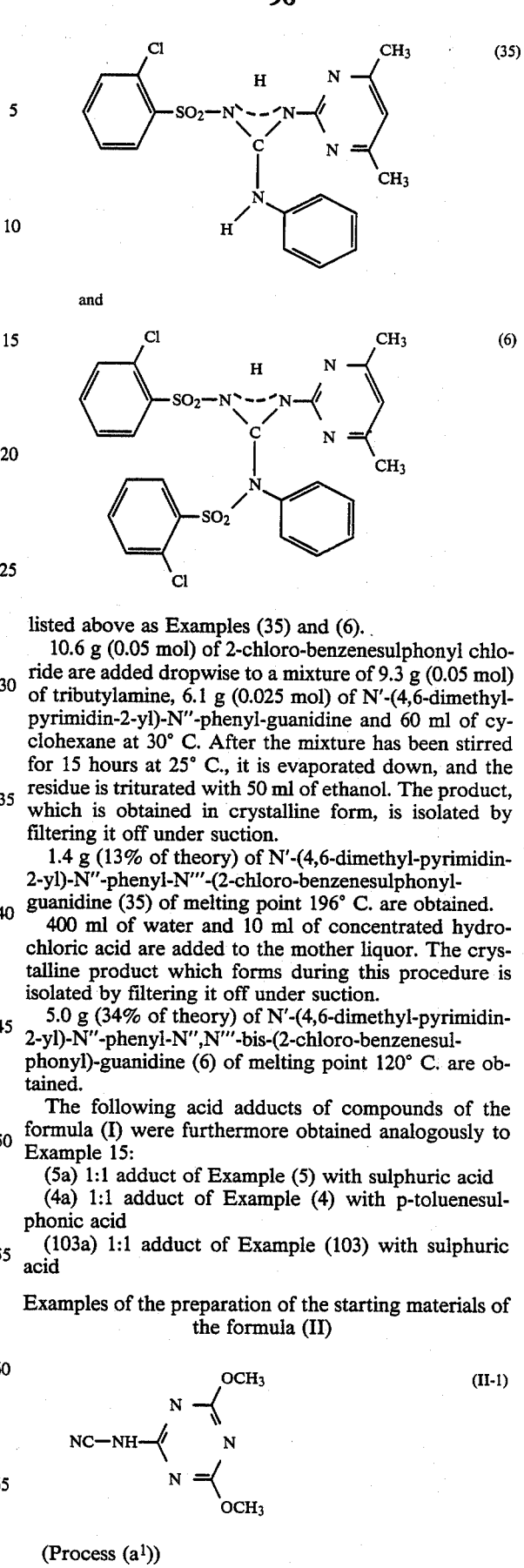

listed above as Examples (35) and (6).

10.6 g (0.05 mol) of 2-chloro-benzenesulphonyl chloride are added dropwise to a mixture of 9.3 g (0.05 mol) of tributylamine, 6.1 g (0.025 mol) of N'-(4,6-dimethyl-pyrimidin-2-yl)-N"-phenyl-guanidine and 60 ml of cyclohexane at 30° C. After the mixture has been stirred for 15 hours at 25° C., it is evaporated down, and the residue is triturated with 50 ml of ethanol. The product, which is obtained in crystalline form, is isolated by filtering it off under suction.

1.4 g (13% of theory) of N'-(4,6-dimethyl-pyrimidin-2-yl)-N"-phenyl-N'''-(2-chloro-benzenesulphonyl)-guanidine (35) of melting point 196° C. are obtained.

400 ml of water and 10 ml of concentrated hydrochloric acid are added to the mother liquor. The crystalline product which forms during this procedure is isolated by filtering it off under suction.

5.0 g (34% of theory) of N'-(4,6-dimethyl-pyrimidin-2-yl)-N"-phenyl-N",N'''-bis-(2-chloro-benzenesulphonyl)-guanidine (6) of melting point 120° C. are obtained.

The following acid adducts of compounds of the formula (I) were furthermore obtained analogously to Example 15:

(5a) 1:1 adduct of Example (5) with sulphuric acid
(4a) 1:1 adduct of Example (4) with p-toluenesulphonic acid
(103a) 1:1 adduct of Example (103) with sulphuric acid Examples of the preparation of the starting materials of the formula (II)

(II-1)

(Process (a¹))

52.7 g (0.3 mol) of 2-chloro-4,6-dimethoxy-s-(-triazine are added to a solution of 30 g (0.3 mol) of disodium cyanamide in 600 ml of acetone, and the reaction mixture is heated at the boil under reflux for 6 hours. After the solvent has been distilled off, the crystalline residue is dissolved in 250 ml of water and the solution is acidified with concentrated hydrochloric acid. The product, which is obtained in crystalline form, is isolated by filtering it off under suction.

33 g (61% of theory) of 2-cyanoamino-4,6-dimethyl-s-triazine having a melting point above 300° C. are obtained.

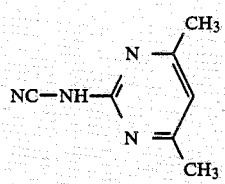
(II-2)

(Process (a²))

A mixture of 42 g (0.5 mol) of cyanoguanidine ("dicyanodiamide") and 50 g (0.5 mol) of 2,4-pentanedione ("acetylacetone") is heated to 120° C. for 15 hours. The reaction mixture is then cooled, after which 500 ml of water are added and the solution is acidified with hydrochloric acid at 0° C. to 10° C. The product obtained in crystalline form during this procedure is isolated by filtering it off under suction. 51.8 g (70% of theory) of 2-cyanoamino-4,6-dimethyl-pyrimidine of melting point 205° C. are obtained.

It was possible to prepare the compounds of the formula (II) listed below in the same manner:

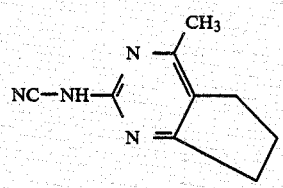
(II-3)

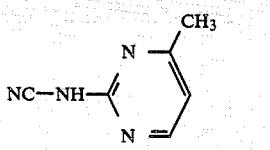
(II-4)

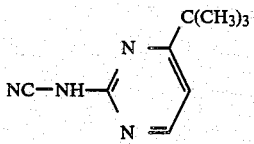
(II-5)

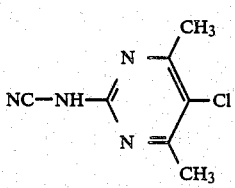
(II-6)

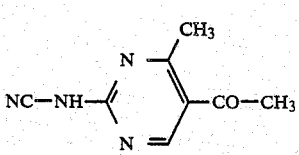
(II-7)

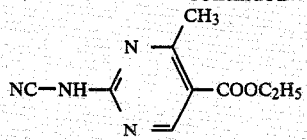
(II-8)

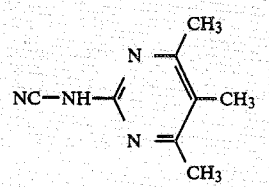
(II-9)

2-(Alkyl-cyano-amino)-pyrimidines of the formula (II) can be prepared, for example, as follows:

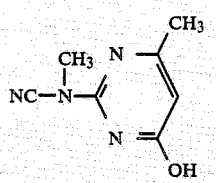
(II-10)

12.6 g (0.1 mol) of dimethyl sulphate are added dropwise to a solution of 15 g (0.1 mol) of 2-cyanoamino-(-4-hydroxy-6-methyl-pyrimidine—prepared by process (a²)—and 4.1 g (0.1 mol) of sodium hydroxide in 60 ml of water, the reaction temperature increasing from 20° C. to 40° C. After the mixture has been stirred for two hours at 20° C., the product, which is obtained in crystalline form, is isolated by filtering it off under suction. 11.1 g (68% of theory) of 2-(methyl-cyano-amino)-4-hydroxy-6-methyl-pyrimidine of melting point 290° C. are obtained.

The following compound is obtained analogously:

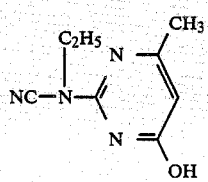
(II-11)

M.p. 215° C. to 220° C.

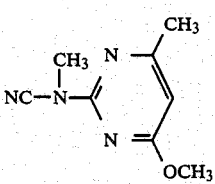
(II-12)

127.5 g (1 mol) of dimethyl sulphate are added dropwise to a solution of 75 g (0.5 mol) of 2-cyanoamino-4-hydroxy-6-methyl-pyrimidine—prepared by process (a²)—and 44 g (1.1 mols) of sodium hydroxide in 750 ml of water, the reaction temperature increasing from 20° C. to 35° C. After the mixture has been stirred for twelve hours at 20° C., the pH value is adjusted to between 9 and 10 by the addition of sodium hydroxide solution, and the product, which is obtained in crystalline form, is isolated by filtering it off under suction.

13 g (15% of theory) of 2-(methyl-cyano-amino)-4-methoxy-6-methyl-pyrimidine of melting point 123° C. are The following compounds are obtained analogously:

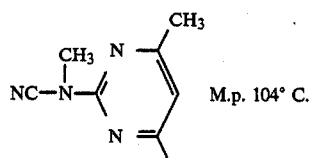  (II-13)  M.p. 104° C.

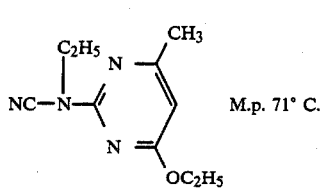  (II-14)  M.p. 71° C.

Examples of the preparation of starting materials of the formulae (IV) and (V):

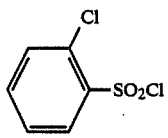  (IV-1)

(Process (b¹))

295 ml of phosphoryl chloride ("phosphorus oxychloride") are added dropwise, at 20° C. to 30° C., to a mixture of 172 g (0.8 mol) of sodium 2-chloro-benzenesulphonate, 300 ml of acetonitrile and 300 ml of sulpholane. The reaction mixture is stirred for 4 hours at 70° C., then cooled to 5° C. and diluted with ice-water. After the mixture has been extracted with petroleum ether, and the extraction solution has been washed with water, dried, filtered and evaporated down, the product remaining in the residue is purified by vacuum distillation 117 g (70% of theory) of 2-chloro-benzenesulphonyl chloride of boiling point 110° C./0.8 mm Hg are obtained.

In the same manner, it was possible to prepare the compounds of the formula (IV) which are listed below:

| | | |
|---|---|---|
| (IV-2) | 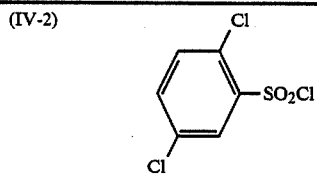 | oil |
| (IV-3) | 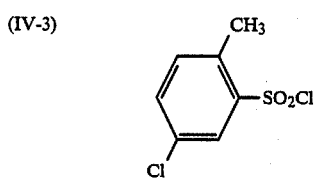 | oil |
| (IV-4) | 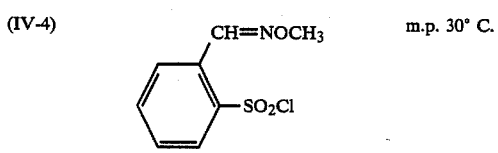 | m.p. 30° C. |

| | | |
|---|---|---|
| (IV-5) | 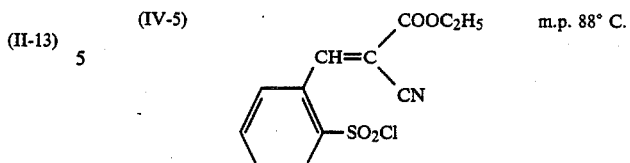 | m.p. 88° C. |
| (IV-6) | 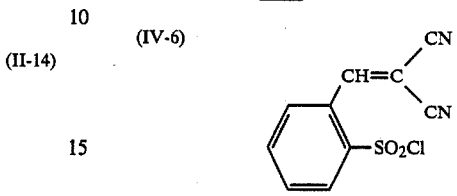 | |
| (IV-7) | 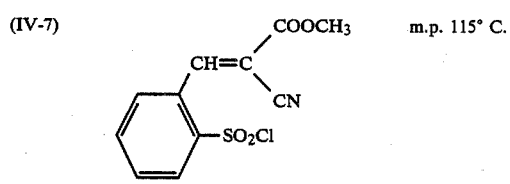 | m.p. 115° C. |
| (IV-8) | 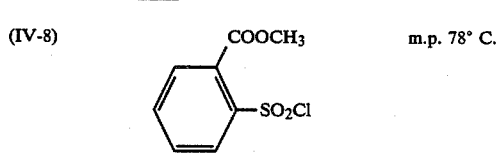 | m.p. 78° C. |

(Process b²))

75.5 g (0.5 mol) of methyl 2-aminobenzoate are dissolved in 176 ml of concentrated hydrochloric acid and 100 ml of acetic acid. A solution of 34.4 g of sodium nitrite in 70 ml of water is added dropwise to this solution at 0° C. After the reaction mixture has been stirred for a further 15 minutes, it is added slowly to a saturated solution, cooled to 0° C., of sulphur dioxide in 450 ml of acetic acid. After the cooling bath has been removed, the mixture is stirred until evolution of gas is complete, 10 g of copper(II) chloride being introduced in portions. After the mixture has been diluted with ice-water and extracted with methylene chloride, and the extraction solution has been washed with water, dried, filtered and evaporated down, the product remaining in the residue is purified by vacuum distillation.

45 g (38% of theory) of 2-methoxy-carbonylbenzenesulphonyl chloride of boiling point 150° C./1 mm Hg are obtained.

In the same manner, it was possible to prepare the compounds of the formula (IV) which are listed below:

| | | |
|---|---|---|
| (IV-9) | 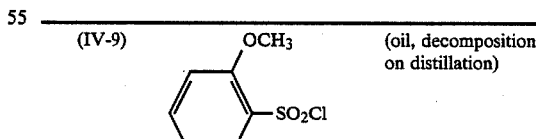 | (oil, decomposition on distillation) |
| (IV-10) | 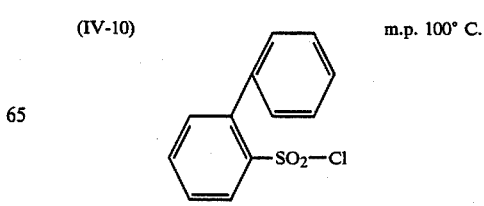 | m.p. 100° C. |

-continued (IV-11) 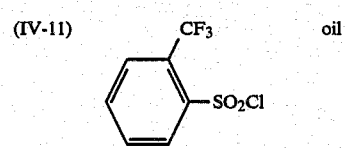 oil (IV-12)  b.p. 142° C./3 mm Hg (IV-13) 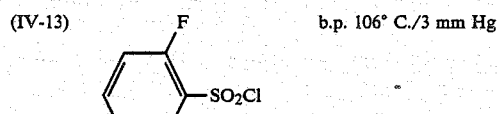 b.p. 106° C./3 mm Hg Examples of the preparation of starting materials of the formula (VI)

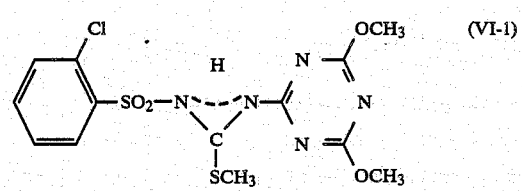 (VI-1)

11 g (0.4 mol) of sodium hydride (80% strength) are added in portions to a suspension of 31.2 g (0.2 mol) of 2-amino-4,6-dimethyl-s-triazine in 200 ml of tetrahydrofuran at 20° C. After the mixture has been stirred for 12 hours, 60 g (0.2 mol) of N-(2-chloro-benzenesulphonyl) S',S"-dimethyl isodithiocarbamate are added, the reaction temperature increasing to 60° C. The reaction mixture is stirred for 5 hours at 20° C., diluted with 800 ml of water and filtered. After acidification with concentrated hydrochloric acid, the product crystallizes and is isolated by filtering it off under suction.

42 g (48% of theory) of N'-(4,6-dimethoxy-s-(-triazin-2-yl)-N"-(2-chloro-benzenesulphonyl)-S-methylisothiourea of melting point 176° C. are obtained.

In the same manner, it was possible to prepare the compounds of the formula (VI) which are listed below:

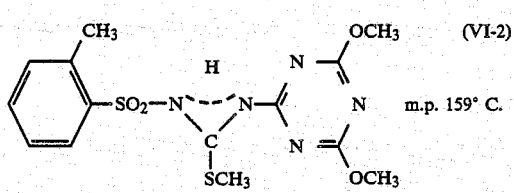 (VI-2) m.p. 159° C.

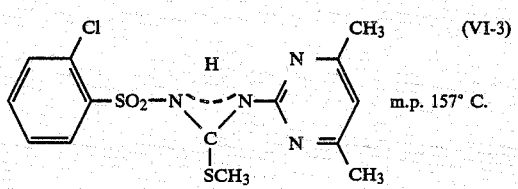 (VI-3) m.p. 157° C.

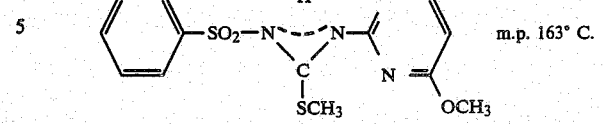 (VI-4) m.p. 163° C.

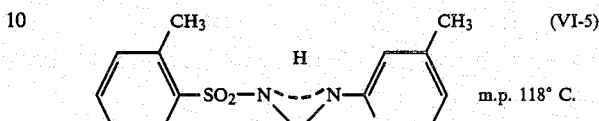 (VI-5) m.p. 118° C.

 (VI-6) m.p. 157° C.

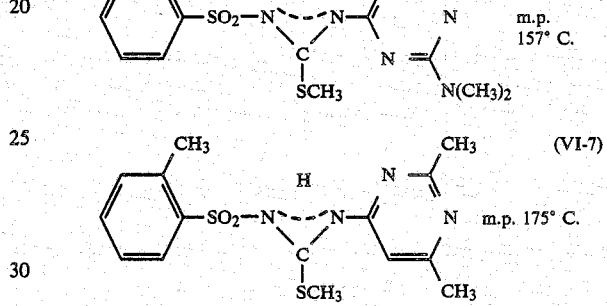 (VI-7) m.p. 175° C.

Examples of the preparation of starting materials of the formula (VIII):

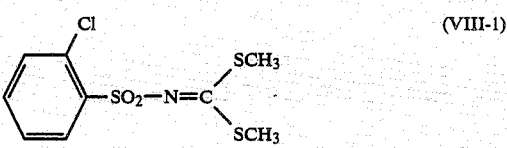 (VIII-1)

8 g (0.2 mol) of sodium hydroxide—dissolved in 15 ml of water—and 6 ml (0.11 mol) of carbon disulphide are simultaneously added dropwise (from different dropping funnels) to a solution of 20 g (0.1 mol) of 2-chlorobenzenesulphonamide in 80 ml of dimethylformamide at 20° C. After the mixture has been stirred for one hour, 13 ml (0.22 mol) of methyl iodide are added dropwise, and the reaction mixutre is stirred for a further hour at 20° C. The product is precipitate by the addition of 500 ml of water, and is isolated by filtering it off under suction.

22.1 g (75% of theory) of N-(2-chloro-benzenesulphonyl) S',S"-dimethyl isodithiocarbamate of melting point 112° C. are obtained.

In the same manner, it was possible to prepare the following compound of the formula (VIII):

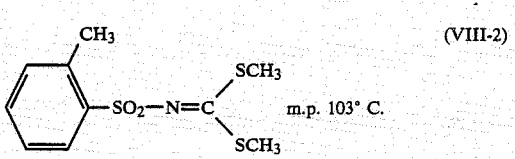 (VIII-2) m.p. 103° C.

USE EXAMPLES

EXAMPLE A

Pre-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)
100%=total destruction

In this test, for example, the following compound from the preparation examples shows an excellent activity: (4).

EXAMPLE B

Inhibition of growth of soybeans
Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Soybean plants are grown in a greenhouse until the first secondary leaf has unfolded completely. In this stage, the plants are sprayed with the preparations of active compound until dripping wet. After 3 weeks, the additional growth is measured on all the plants and the inhibition of growth in percent of the additional growth of the control plants is calculated. 100% inhibition of growth means that growth has stopped and 0% denotes a growth corresponding to that of the control plants.

In this test, for example, the following compound according to the preparation examples shows an excellent activity: (4).

EXAMPLE C

Inhibition of growth of barley
Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Barley plants are grown in a greenhouse to the 2-leaf stage. In this stage, the plants are sprayed with the preparations of active compound until dripping wet. After 3 weeks, the additional growth is measured on all plants and the inhibition of growth in percent of the additional growth of the control plants is calculated. 100% inhibition of growth means that growth has stopped and 0% denotes a growth corresponding to that of the control plants.

In this test, for example, the following compounds according to the preparation examples show an excellent activity: (4), (16), (72), (73), (74), (75), (77), (78), (79) and (80).

EXAMPLE D

Inhibition of growth of cotton
Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Cotton plants are grown in a greenhouse until the 5th secondary leaf has unfolded completely. In this stage, the plants are sprayed with the preparations of active compound until dripping wet. After 3 weeks, the additional growth of the plants is measured and the inhibition of growth in percent of the additional growth of the control is calculated. 100% inhibition of growth means that growth has stopped and 0% denotes a growth corresponding to that of the control plants.

In this test, for example, the following compound according to the preparation examples shows an excellent activity: (4).

It is understood that the specification and examples are illustrative but not limitative of the present invention and that other embodiments within the spirit and scope of the invention will suggest themselves to those skilled in the art.

In the following claims, "plant growth" includes increasing or decreasing growth or even terminating it altogether as in herbicidal activity.

We claim:

1. A process for the preparation of a guanidine derivative of the formula

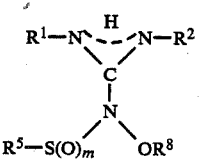

in which
$R^1$ represents hydrogen or the radical $R^5-S(O)_m-$,
m represents the numbers zero, 1 or 2 and
$R^5$ represents a radical selected from the group consisting of alkyl aralkyl, pyridyl, quinolinyl, furyl, thienyl and pyrrolyl,
$R^2$ represents a six-membered aromatic heterocyclic structure selected from the group consisting of pyridyl, pyrimidinyl and 1,3,5-triazinyl and which is substituted by halogen, amino, cyano or formyl and/or by optionally substituted radicals from the group consisting of alkyl, alkoxy, alkylamino, dialkylamino, alkylcarbonyl and alkoxycarbonyl, and
$R^8$ represents an optionally substituted radical from the group consisting of $C_1-C_6$-alkyl, alkenyl, alkinyl, cycloalkyl, phenylallkyl and aryl,
which comprises reacting a guanidine derivative of the formula

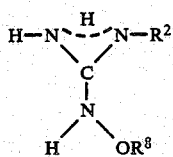

with one or two molar equivalent(s) respectively, of a halogen/sulphur compound of the formula

in which

X¹ represents fluorine, chlorine or bromine.

2. A process according to claim 1 for the preparation of a guanidine derivative of the formula

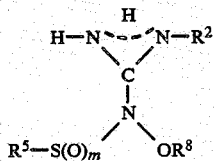

which comprises reacting a guanidine derivative of the formula

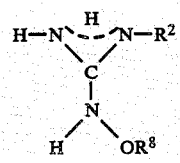

with about an equimolar amount of $R^5\text{—S(O)}_m\text{—X}^1$.

3. A process according to claim 1 for the preparation of a guanidine derivative of the formula

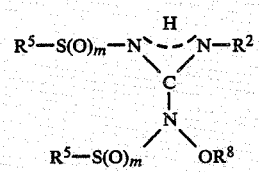

which comprises reacting a guanidine derivative of the formula

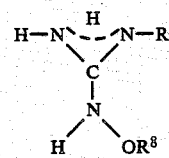

with at least two molar equivalents of $R^5\text{—S(O)}_m\text{—X}^1$ or reacting a guanidien derivative of the formula

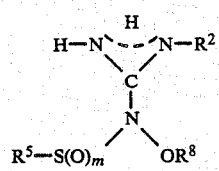

with at least one molar equivalent of
$R^5\text{—S(O)}_m\text{—X}^1$.

4. The process according to claim 1, wherein $R^5$—S(O)$_m$—X¹ is selected from the group consisting of 2-chloro-, 2-fluoro-, 2-bromo-, 2-nitro-, 2-methyl-, 2-methoxycarbonyl-, 2-ethoxycarbonyl-, 2-methoxy-, 2-ethoxy-, 2-phenyl-, 2-trifluoromethyl-, 2-difluoromethoxy-, 2-trifluoromethoxy-, 2-phenoxy-, 2-methyl-5-chloro-, 2,5-dichloro- and 2-chloro-5-trifluoromethyl-benzenesulphonyl chloride.

5. The process according to claim 1, wherein the reaction is effected in an organic solvent.

6. The process according to claim 1, wherein the reaction is effected in an aprotic polar solvent.

7. The process according to claim 1, wherein the reaction is effected in at least one solvent selected from the group consisting of a hydrocarbon, a halogenated hydrocarbon, a nitrile, dimethyl formamide, dimethyl acetamide, dimethyl sulphoxide, sulpholane, hexamethylphosphoric acid triamide, 1,2-dimethoxyethane, pyridine and 2-methyl-5-ethylpyridine.

8. The process according to claim 1, wherein the reaction is effected in the presence of an acid-binding agent.

9. The process according to claim 1, wherein the reaction is effected in the presence of an acid-binding agent selected from the group consisting of alkali metal and alkaline earth metal hydroxides or hydrides, organometallic compounds, and organic amines.

10. The process according to claim 1, wherein the reaction is effected in the presence of an acid-binding agent selected from the group consisting of trimethylamine, triethylamine, N,N-dimethylaniline, N,N-dimethyl-benzylamine, diazabicyclooctane (DABCO), diazabicycloundecene (DBU), pyride and 2-methyl-5-ethyl-pyridine.

11. The process according to claim 1, wherein the reaction is effected in the presence of diazabicyclooctane (DABCO) as an acid-binding agent.

* * * * *

UNITED STATES PATENT AND TRADEMARK OFFICE
CERTIFICATE OF CORRECTION

PATENT NO. : 4,797,484

DATED : January 10, 1989

INVENTOR(S) : Koichi Moriya, et al

Page 1 of 4

It is certified that error appears in the above-identified patent and that said Letters Patent is hereby corrected as shown below:

| | |
|---|---|
| Col. 12, line 48 | Correct spelling of --alkanesulphonic-- |
| Col. 13, line 53 and Col. 16, line 49 | After "$R^5$," insert --wherein-- |
| Col. 16, line 30 | Before "radical" delete "o" and substitute --or the-- |
| Col. 17, line 15 | After "$R^6$," insert --wherein-- |
| Col. 18, line 9 | After formula insert --wherein-- |
| Col. 19, line 28 | After "If" insert --,-- |
| Col. 19, line 48 | Delete "$H_2N(C_2H_5)$" and substitute --$H_2N(C_2H_5)_2$-- |
| Col. 21, line 46 | Middle of formula delete "C" and substitute 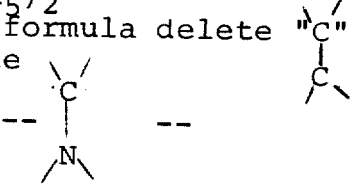 |
| Col. 21, line 52 | Delete formula and substitute --$R^5-S(O)_m-X^1$-- |
| Col. 22, line 40 | After "cyanoamino-4-methyl-" and before "2-(cyano-N-methyl-" insert --6-isobutoxypyrimidine,-- |
| Col. 22, line 45 | Delete "striazine" and substitute --s-triazine-- |
| Col. 23, lines 19-20 | Delete "dioxahe" and substitute --dioxane-- |
| Col. 23, line 41 | Delete "$C_1-C_4$-alkoxy" and substitute --$C_1-C_4$-alkyl-- |

UNITED STATES PATENT AND TRADEMARK OFFICE
CERTIFICATE OF CORRECTION

PATENT NO. : 4,797,484
DATED : January 10, 1989
INVENTOR(S) : Koichi Moriya, et al It is certified that error appears in the above-identified patent and that said Letters Patent is hereby corrected as shown below:

| | |
|---|---|
| Col. 23, lines 63-64 | Delete "phenylene diamine" and substitute --phenylenediamine-- |
| Col. 24, line 51 | End of line delete "(4-l" and substitute --4- -- |
| Col. 24, line 54 | Before "dimethyl" insert --N'-(4,6- -- |
| Col. 24, line 55 | Delete "riazin" and substitute --triazin-- |
| Col. 24, line 55 | Delete "2-y" and substitute --2-yl-- |
| Col. 24, line 59 | Delete "pyrimidine" and substitute --pyrimidin-2- -- |
| Col. 25, line 10 | Delete "guaridine" and substitute --guanidine-- |
| Col. 28, line 24 | Delete "is" and substitute --as-- |
| Col. 29, line 48 | Delete "iven" and substitute --given-- |
| Col. 31, line 22 | Delete "addin" and substitute --adding-- |
| Col. 33, line 50 | Delete "eneral" and substitute --general-- |
| Col. 34, line 26 | Delete "rowth" and substitute --growth-- |
| Col. 34, line 28 | Delete "row" and substitute --grow-- |
| Col. 35, line 46 | Delete "reater" and substitute --greater-- |
| Col. 41, line 45; and Col. 43, line 11 | Insert --and-- |

UNITED STATES PATENT AND TRADEMARK OFFICE
CERTIFICATE OF CORRECTION

PATENT NO. : 4,797,484
DATED : January 10, 1989
INVENTOR(S) : Koichi Moriya, et al It is certified that error appears in the above-identified patent and that said Letters Patent is hereby corrected as shown below:

| | |
|---|---|
| Col. 42, line 62 | Delete "ttirred" and substitute --stirred-- |
| Col. 43, line 44; and Col. 44, line 17 | Correct --chloro-benzenesulphonyl-- |
| Col. 44, line 15 | After "Process d)" delete "po" and start new paragraph |
| Col. 44. line 43 | Before "hours" insert --3-- |
| Col. 95, lines 53, and 66 | Delete "N,-(4-" and substitute --N'-(4- -- |
| Col, 95, line 67 | Delete "N",N" " and substitute --N",N"'-- |
| Col. 96, line 58 | Delete "[2.2]" and substitute --[2.2.2]-- |
| Col. 97, line 19 | Correct --diazabicyclo- -- |
| Col. 97, line 60 | Before "minutes" insert --10-- |
| Col. 99, line 1 | Delete "52 7" and substitute --52.7-- |
| Col. 100, line 35 | Delete "11 1" and substitute --11.1--(which should start new paragraph) |
| Col. 100, line 68 | After "are" insert --obtained-- |
| Col. 101, line 40 | After "distillation" insert --.-- |
| Col. 104, line 51 | Correct spelling of --mixture-- |
| Col. 104, line 52 | Delete "precipitate" and substitute --precipitated-- |
| Col. 106, line 52 | Delete "$R_1$" and substitute --$R^1$-- |

UNITED STATES PATENT AND TRADEMARK OFFICE
CERTIFICATE OF CORRECTION

PATENT NO. : 4,797,484

DATED : January 10, 1989

INVENTOR(S) : Koichi Moriya, et al

It is certified that error appears in the above-identified patent and that said Letters Patent is hereby corrected as shown below:

| | |
|---|---|
| Col. 106, line 55 | After "aralkyl," insert --aryl-- |
| Col. 106, line 66 | Correct spelling of --phenylalkyl-- |
| Col. 108, line 13 | Correct --guanidine-- |
| Col. 108, line 56 | Delete "pyride" and substitute --pyridine-- |

Signed and Sealed this

Seventeenth Day of April, 1990

Attest:

HARRY F. MANBECK, JR.

*Attesting Officer*     *Commissioner of Patents and Trademarks*

UNITED STATES PATENT AND TRADEMARK OFFICE
CERTIFICATE OF CORRECTION

PATENT NO. : 4,797,484

DATED : January 10, 1989

INVENTOR(S) : Koichi Moriya, et al

It is certified that error appears in the above-identified patent and that said Letters Patent is hereby corrected as shown below:

Col. 11, line 27    Delete "fluoromethoxy" and substitute --trifluoromethoxy--

Signed and Sealed this

Fifteenth Day of January, 1991

Attest:

HARRY F. MANBECK, JR.

*Attesting Officer*   *Commissioner of Patents and Trademarks*